United States Patent [19]
Kim et al.

[11] Patent Number: 5,879,900
[45] Date of Patent: *Mar. 9, 1999

[54] METHOD FOR SIMULTANEOUS ANALYSIS OF CELL VIABILITY, NUCLEATED RED BLOOD CELLS AND WHITE BLOOD CELL DIFFERENTIALS

[75] Inventors: Young Ran Kim; Michael W. Yee, both of Sunnyvale; Suresh N. Mehta, Pleasanton; Josefino C. Sagala, San Jose, all of Calif.

[73] Assignee: Abbott Laboratories, Abbott Park, Ill.

[*] Notice: The term of this patent shall not extend beyond the expiration date of Pat. No. 5,590,037.

[21] Appl. No.: 851,526

[22] Filed: May 5, 1997

Related U.S. Application Data

[63] Continuation of Ser. No. 574,424, Dec. 15, 1995, abandoned, which is a continuation-in-part of Ser. No. 356,932, Dec. 15, 1994, Pat. No. 5,559,037.

[51] Int. Cl.$^6$ .................................................. G01N 33/569
[52] U.S. Cl. .......................... 435/724; 436/536; 436/164; 436/172; 530/413; 356/39
[58] Field of Search ............................ 435/7.24; 436/536, 436/547, 548, 8, 10, 13, 43, 52, 53, 63, 66, 164, 172, 174, 175, 800; 530/413; 424/534, 151–154.1; 356/39

[56] References Cited

U.S. PATENT DOCUMENTS

| | | |
|---|---|---|
| 4,284,412 | 8/1981 | Hansen et al. . |
| 4,492,752 | 1/1985 | Hoffman et al. . |
| 4,520,110 | 5/1985 | Stryer et al. . |
| 4,544,546 | 10/1985 | Wang et al. . |
| 4,661,913 | 4/1987 | Wu et al. . |
| 4,727,020 | 2/1988 | Recktenwald et al. . |
| 4,751,179 | 6/1988 | Ledis et al. . |
| 4,751,188 | 6/1988 | Valet . |
| 4,882,284 | 11/1989 | Kirchanski . |
| 4,978,624 | 12/1990 | Cremins et al. . |
| 4,986,657 | 1/1991 | Ohe . |
| 4,987,086 | 1/1991 | Brosnan et al. . |
| 5,047,321 | 9/1991 | Loken et al. . |
| 5,057,413 | 10/1991 | Terstappen et al. . |
| 5,125,737 | 6/1992 | Rodriguez et al. . |
| 5,188,935 | 2/1993 | Leif et al. . |
| 5,298,426 | 3/1994 | Inami et al. . |
| 5,559,037 | 9/1996 | Kim et al. . |
| 5,627,037 | 5/1997 | Ward et al. . |

FOREIGN PATENT DOCUMENTS

| | | |
|---|---|---|
| 0022670 | 1/1981 | European Pat. Off. . |
| 0105614 | 4/1984 | European Pat. Off. . |
| 0121261 | 10/1984 | European Pat. Off. . |
| 0559208 | 9/1993 | European Pat. Off. . |
| 9418828 | 9/1994 | WIPO . |

OTHER PUBLICATIONS

Bakker–Schut et al., *Computers and Biomedical Research*, vol. 27, No. 2, (1994), pp. 83–96.

Leary et al., *Journal of Histochemistry and Cytochemistry*, vol. 24, No. 12, (1976), pp. 1249–1257.

*Primary Examiner*—Paula K. Hutzell
*Assistant Examiner*—Heather A. Bakalyar
*Attorney, Agent, or Firm*—Richard D. Schmidt; Dianne Casuto; Mimi C. Goller

[57] ABSTRACT

A method for the simultaneous and quantitative, flow cytometric analysis of nucleated red blood cells (NRBC), white blood cells (WBC), damaged white blood cells and a white blood cell subclass differential (WBC/Diff) is provided. The method includes mixing an aliquot of a whole blood sample with a reagent system comprising a red blood cell (RBC) lysing component which lyses RBCs and NRBCs while minimizing damage to WBC cellular membranes and a membrane-impermeant nucleic acid stain which stains exposed NRBC nuclei and damaged WBCs, subjecting the stained aliquot to flow cytometric light measurements, obtaining at least one signal for the parameters of fluorescence (FL) and scattered light at a first and a second range of scatter angles, qualifying the obtained signals using AND/OR logic wherein to be qualified, a signal must be greater than the second scatter signal threshold AND also greater than either the first scatter signal threshold OR the FL threshold, constructing a three-dimensional plot of qualified intensity signals of fluorescence and scattered light from the detected signals, and differentiating the NRBC, WBC, damaged WBC and WBC/Diff from the constructed three-dimensional plot and determining the number of cells of each.

5 Claims, 21 Drawing Sheets

METHOD FOR SIMULTANEOUS ANALYSIS OF CELL VIABILITY, NUCLEATED RED BLOOD CELLS AND WHITE BLOOD CELL DIFFERENTIALS

REFERENCE TO RELATED APPLICATIONS

This application is a File Wrapper Continuation of application Ser. No. 08/574,424, filed Dec. 15, 1995, now abandoned, which is a continuation-in-part application of Ser. No. 08/356,932, filed on Dec. 15, 1994, entitled "METHOD FOR RAPID ANALYSIS OF NUCLEATED RED BLOOD CELLS", now U.S. Pat. No. 5,559,037 and is incorporated herein in its entirety by this reference.

BACKGROUND OF THE INVENTION

This invention relates to a method for the simultaneous and quantitative analysis of damaged white blood cells (WBC), nucleated red blood cells (NRBC) and white blood cell sub-populations (WBC/Diff). More particularly this invention relates to differentiating WBC, NRBC, damaged WBC a WBC subclass differential (WBC/Diff) in a whole blood sample by the use of multi-dimensional light scatter and fluorescence analysis and a lysing reagent capable of lysing red blood cells (RBC) without damaging WBC cellular membranes.

NRBC counts are conventionally determined by means of blood smear morphology. A stained blood smear is examined under the microscope and the NRBC are manually counted. In general, an NRBC concentration is reported as number of NRBC per 100 white blood cells ("WBC"). Normally, 200 WBC and the number of NRBC present in the same region on a patient blood smear are counted and the numbers are divided by 2 to express the NRBC concentration as the number of NRBC/100 WBC. The major drawback to this type of manual microscopic method is that it is very labor intensive, time-consuming, subjective and inaccurate due to poor statistics. Therefore, an accurate automated NRBC method has long been sought after by pathologists and laboratory technicians.

A major problem in automating a NRBC method for use on a clinical flow cytometer has been that since NRBC are rare events and RBC populations are so numerous, NRBC populations are not easily detected among the red blood cell ("RBC") population by either the differences in the cell's electrical resistivity (impedance measurements) or its light scattering characteristics (optical measurements). Although many attempts have been made to count NRBC among WBC populations, instead of among RBC population, these efforts have not generally been successful.

NRBC populations are not easily distinguished from WBC populations since NRBC do not form a well defined cluster among the WBC in the usual two dimensional space differentiation methods utilized on flow cytometers. One is usually not able to separate NRBC populations from the lymphocyte populations when the detected signals are viewed on the generally accepted, two-dimensional light scatter (forward vs. side) or light scatter vs. absorption, dot plots. The signals from the majority of the NRBC population is usually mixed in with the signals for RBC stroma and platelets ("PLT"), and the upper-end of NRBC cluster most often will extend into the space occupied by the lymphocyte population.

Automated clinical hematology instruments, such as the Technicon H*1®, Coulter STK® S and Abbott Cell-Dyn® 3000 and 3500 instruments only "flag" samples for the possible presence of NRBC if the sample dot plot shows increased noise signals below the lymphocyte cluster. This type of flagging very often produces false positive results since the elevated noise level could be due to PLT clumps, giant PLT or incompletely lysed RBC. In addition, it is extremely difficult to obtain an accurate Total WBC count and WBC Differential ("WBC/Diff") on samples containing NRBC because of the interference. Additionally, blood smears of the flagged samples must be examined and counted under the microscope by a skilled technician to obtain accurate WBC differential and NRBC counts. This is a very labor-intensive and subjective process.

Notwithstanding these difficulties, the identification and quantitation of damaged cells among intact cells in a sample may be of importance for accurate characterization of cell populations exhibiting spontaneous cell death or cells affected by cytotoxic agents or cancer drugs. Nonviable cells may bind antibodies or other cellular markers non-specifically, and therefore should be identified and quantified in immuno-phenotyping as well as from hematology analysis.

In vivo, there are two different forms of cell death: apoptosis and necrosis. Apoptosis, the term introduced by Kerr et al., is a genetically programmed cell death which takes place during metamorphosis, embryogenesis, and morphogenesis. neutrophils undergo apoptosis during the inflammatory reaction, lymphocytes in the regulation of the immune system. Cell injury due to a variety of agents including chemotherapeutic cytotoxic insults may also lead to apoptosis. Apoptosis has also been demonstrated in pre-malignant and malignant tissues. During the process of apoptosis, the cell membrane remains intact and the cell breaks into apoptotic bodies which are then phagocytosed. Necrosis, or accidental cell death, on the other hand, occurs in response to harmful insults such as physical damage, hypoxia, hyperthermia, starvation, complement attack and chemical injury. These cells lose ability to selectively permeate extracellular materials and leak, finally losing their plasma membrane. Cells that have lost plasma membrane integrity become permeable to external compounds such dyes that normally will not penetrate the intact cell membrane are considered to be "nonviable" or damaged. Damaged cells which have lost their plasma membrane integrity also do not function metabolically.

In vitro, a similar phenomenon, cell death, occurs as a blood sample ages or during cell preparation procedures that damage the cell prior to flow cytometric analysis. Current cell preparation procedures subject the cells to a long process including labelling cells with monoclonal antibodies (Mab), lysing of red blood cells (RBC) and fixing of the white blood cells (WBC) to prevent further destruction.

The combination of 90° and forward light scatter techniques have been used in the art to discriminate damaged cells from intact cells. It has been found however, that light scatter alone is not sensitive enough to clearly separate and quantitate the damaged or nonviable cells from the viable or intact cells. This is particularly true if a sample contains heterogenous cell populations such as a blood sample. Use of a fluorescent nucleic acid stain in addition to multi-angle light scatter dramatically increases the sensitivity of the detection for dead cells.

Currently a variety of techniques exist utilizing light scatter and fluorescence techniques for determining whether a cell in a sample is intact or damaged. According to the art viable, intact cells can be distinguished from dead cells by using either fluorescein diacetate (FDA) or propidium iodide (PI). In these methods, the sample is treated with either FDA or PI. The cells which stain with FDA are considered viable and the cells which stain with PI are considered "dead". However, these methods are limited in that the cells cannot be fixed since fixed cells generate autofluorescence. In addition, fluorescein, which is a product of FDA post hydrolysis by intracellular esterase, is so bright that it overwhelms the immunofluorescence signals from other stains such as FITC or phycoerythrin (PE).

U.S. Pat. Nos. 4,661,913 and 4,284,412 describe methods of differentiating WBC subpopulations by light scatter analysis on a flow cytometer. U.S. Pat. No. 4,520,110 describes a method of differentiating heterogenous leukocyte populations by immuno-phenotyping using a combination of light scatter and fluorescence. Each of the above described methods require manual sample preparation and incubation time much too long to be incorporated on a rapid multi-parameter hematology analyzer of today. Additionally, these references do not appear to teach how to discriminate damaged cells from intact cells.

U.S. Pat. No. 4,751,188, to Valet, describes a method which is based on the principle that cellular components can be stained by dyes and measured simultaneously with cell volume, for example in a flow cytometer. According to the patent a complete blood count can be produced within a few minutes. In this method, a blood sample is manually prepared by a procedure that comprises the steps of: making a 1:250 dilution of the sample with buffered isotonic saline; adding 5 microliters of a predetermined concentration of a stock solution which contains a fluorescent RNA/DNA stain, a fluorescent membrane-potential-sensitive stain, fluorescing monodisperse calibration particles and an organic solvent in which the dyes dissolve; and incubating the mixture at room temperature for 3 to 5 minutes. The dyes are stored in an organic solvent such as DMSO or DMF as a stock solution and only a very small amount of these stock dye solutions are added directly to the cell suspension to stain the cells. The prepared cell suspension is then aspirated through flow cytometer flow cell for measurement. In this method, a DNA/RNA stain is used. This DNA/RNA stain is either acridine orange (AO), quinacrine (QA), or pyonine Y (PY) and the membrane-sensitive stain is 3,3-dehexyl-oxacarbocyanine (DiOC6). Additionally, at least one additional stain is used, being selected from the group of: cell protein stains; lipid stains; enzyme stains; intracellular pH stains; and SH group stains. The methodology of Valet, as described in this patent: 1) is not fully automatable because of the step required for manual addition of a very small volume of dye dissolved in organic solvents; 2) is relatively long, as the amount of time necessary to complete the blood cell counts; 3) requires at least two dyes to characterize the blood cell this may produce a problem of quenching; 4) the requirement of making a 250 fold dilution of a blood sample does not provide enough WBC's to produce statistically satisfactory results unless the counting time is much prolonged; 5) does not demonstrate that it is possible to separate monocytes, eosinophils and basophils, suggesting that the teachings of Valet can only produce an incomplete WBC differential results (only two WBC subpopulations, granulocytes and lymphocytes, are shown in the figures and examples).

U.S. Pat. No. 5,057,413, to Terstappen, discloses a flow cytometric method for discriminating between intact and damaged cells. In this method both intact and damaged cells in a sample are stained. The teachings of Terstappen are based upon the principle that there is a sufficient difference in the fluorescent intensity of the stained intact cells and that of damaged cells. A further stated objective of the disclosure is to use the differentiation methods of the art in conjunction with monoclonal antibodies (Mabs) fluorescently labelled with FITC or PE to simultaneously identify cellular antigens, intact cell and damaged cells, wherein the peak emission spectra of each fluorescent label must be distinguishable from each other and from a nucleic acid dye. In this method, RBC's are lysed with ammonium chloride for 3 to 5 minutes, and centrifuged at 200 g for 5 minutes. The pellet was washed twice with RPMI 1640 culture medium, each time centrifuging at 200 g for 5 minutes. And then the cells were resuspended in phosphate buffered saline (PBS) with 1% bovine serum albumin (BSA). When Mabs are added to the sample, incubated 20 minutes on ice, the cells were washed twice with the PBS solution and the cells were resuspended in 1 ml of 1% paraformaldehyde in PBS. A stock solution of LDS-751 was made in methanol and the working solution was prepared by diluting the stock solution in PBS. Ten microliters of this working solution is added to the prepared cell suspension. In another experiment, unfixed WBC's, post ammonium chloride lyse of RBC's, were resuspended and kept in RPMI solution for 1 hour before analysis in order to obtain optimal light scattering properties of the cells.

The Terstappen method has several problems in that may variable in the fixation process, such as temperature, concentration of the fixative(s) and the duration of the fixation, can change the permeability of the cell membrane and thus the intensity of the staining. The hard fixed, originally intact cells may have the same staining intensity as that of the hard fixed, damaged cells since the DNA content of all cells of the same individual is the same (proliferating hyperploidy tumor or leukemic cells are exceptions). In addition, if any DNA fragmentation occurs at the late stage of cell death, then the damaged cells will contain less DNA and the staining intensity will decrease. The Terstappen method is also long and cumbersome making it an difficult, if not impossible to incorporate onto a fully automated hematology instrument of today. The results reported in the patent also indicate that a large portion of the damaged cells may have occurred during the required long and torturous sample preparation procedure.

Recently, U.S. Pat. No. 5,298,426, issued on Mar. 29, 1994, to Inami et al. for the detection of NRBC. This patent teaches a two-step method comprising the staining of WBC and NRBC by specific nuclear stains. In this patented method, a blood sample is first mixed with an acid hypotonic solution containing a fluorescent nuclear dye. Then, a solution comprising an alkaline salt buffer, to adjust pH and Osmolarity, is mixed with the sample/first reagent solution. This final solution is then loaded into a flow cytometer to detect and count NRBC along with other nucleated cells.

There are several reasons why the Inami et al. approach is not acceptable, especially for an automatable method. First, an acidic-hypotonic solution damages all cell membranes making the WBC leaky and therefore selective staining of NRBC nuclei by a nuclear stain is not possible. There are no known dyes which stain only NRBC nuclei and not WBC nuclei since the nuclear material (DNA) is the same. The nuclear stain claimed by Inami et al., is Propidium Iodide, a commonly used nucleic acid stain.

Additionally, the Inami et al. method does not separate or distinguish the fluorescent signals of the NRBC nuclei from that of other nuclear remnants such as Howell-Jolly Bodies, Basophilic Stippling, RNA from lysed reticulocytes and reticulated platelets, and DNA from WBC and Megakaryocytic fragments. Third, the Inami et al. method requires that the sample be pretreated, off-line, using several reagents to "prep" the sample before the prepped sample/reagent solution can be loaded into the instrument.

The problems in the existing art described above have been resolved in the present invention.

Accordingly, an object of the present invention is to provide an accurate method of distinguishing damaged WBC's from intact WBC's, and for rapidly quantitating the WBC differential (WBC/Diff), NRBC's, and damaged WBC's in a whole blood sample.

Another objective of the present invention is to provide a fully automatable method for distinguishing damaged WBC's from intact WBC's, and for rapidly quantitating the WBC/Diff, NRBC's, and damaged WBC's in a whole blood sample.

Yet another object of the present invention is to provide an automated method for distinguishing damaged WBC's from intact WBC's, and for rapidly quantitating the WBC/Diff, NRBC's, and damaged WBC's in a whole blood sample and for immuno-phenotyping.

SUMMARY OF THE INVENTION

A method for the simultaneous and quantitative, flow cytometric analysis of nucleated red blood cells (NRBC) and white blood cells (WBC), damaged or nonviable WBC and subpopulations of white blood cells (WBC/Diff) in a whole blood sample is provided. The method comprises the destruction of RBC and NRBC cytoplasm from an aliquot of a whole blood sample to expose the NRBC nuclei and the nuclei of nonviable cells to a nucleic acid stain that does not permeate intact cell membrane (vital stain) while minimizing or eliminating the permeation of the vital stain into the WBC, subjecting the stained aliquot to flow cytometric light measurements, obtaining at least one signal for parameters including scattered light at a first and a second range of scatter angles and fluorescence (FL), qualifying the obtained signals by using the combination logic wherein a qualified signal must be greater than the second scatter signal threshold, while at the same time it must be greater than either the first scatter signal threshold or the FL threshold {[(first scatter angle signal OR FL signals) AND second scatter angle signal]}, constructing a three-dimensional plot of qualified intensity signals of fluorescence and scattered light from the detected signals, and differentiating the NRBC and WBC, or damaged WBC from the constructed three-dimensional plot and determining the number of cells of each.

In another embodiment of the invention, a device is provided for the simultaneous and quantitative analysis of NRBC, WBC, WBC/Diff and nonviable cells in a whole blood sample. The device comprises a flow cytometer for obtaining at least one signal for parameters including scattered light at a first and a second range of scatter angles and fluorescence (FL or Fl), and a triple triggering circuit that qualifies signals obtained by the flow cytometer for digitation by means of AND/OR logic wherein a qualified signal must be greater than the second scatter signal threshold, while at the same time it must be greater than either the first scatter signal threshold or the FL threshold {[(first scatter angle signal OR FL signals) AND second scatter angle signal]}.

In another embodiment of the invention, a method for the simultaneous and quantitative analysis of NRBC, WBC and WBC/Diff in a whole blood sample is provided. The method comprises the elimination of the red blood cells ("RBC") and the cytoplasm of NRBC from an aliquot of a blood sample to expose the NRBC nuclei, staining the NRBC nuclei and nonviable WBC with a vital stain while minimizing the staining of viable WBC, subjecting the aliquot to flow cytometric light measurements, obtaining at least one signal for parameters including scattered light extinction at from about 0° to about 1° (ALL), scattered light from about 3°–10° (IAS) and fluorescence (Fl), qualifying the signals obtained by using AND/OR logic wherein the logic comprises [(ALL signals) OR (Fl signals) AND (3°–10° scatter signals)], constructing a three-dimensional plot of qualified intensity signals of fluorescence and scattered light from the detected signals, and differentiating nonviable from viable cells and the NRBC, WBC and WBC/Diff, all from the constructed three-dimensional plot and determining the number of cells of each.

In another embodiment of the invention, a flow cytometric device is provided for the quantitative analysis of nonviable cells, NRBC, WBC and WBC/Diff in a whole blood sample. The device comprises a flow cytometer for obtaining at least one signal for parameters including scattered light at from about 0° to about 1° and from about 3°–10° and fluorescence (Fl) and a triple triggering circuit that qualifies signals obtained by the flow cytometer for digitation by means of AND/OR logic wherein the logic comprises [(0° to about 1° scatter signals) OR (Fl signals) AND (3°–10° scatter signals)] to validate signals for further processing.

These and further features and advantages of the invention will be apparent from the following description of the preferred embodiments thereof.

DETAILED DESCRIPTION OF THE INVENTION

Figure 1:
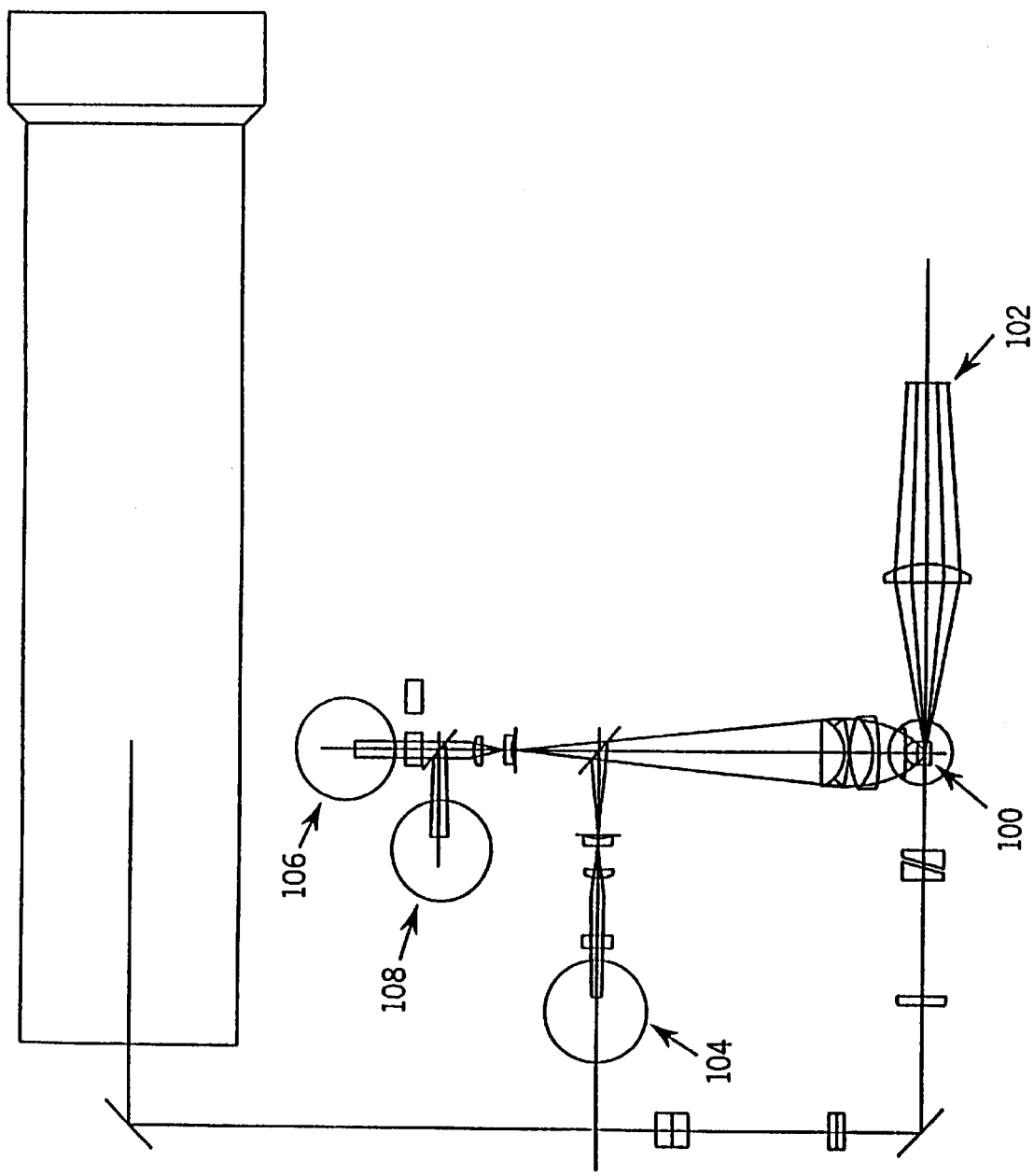
FIG. 1 is a schematic diagram of the optics of a clinical flow cytometer that may be employed in implementing the method of the present invention.

Broadly, the present invention relates to an automated method for simultaneous analysis of WBC differential (Diff), NRBC and cell viability in a whole blood sample.

One aspect of the present invention is that the method utilizes a lysing reagent/dye system in which RBCs and the cytoplasm of NRBC are lysed while minimizing the damage to WBC cellular membranes, and preferably WBC surface antigens, the exposed NRBC nuclei and any damaged WBC nuclei are stained with a nucleic acid stain that does not permeate intact cell membrane (vital stain). Intact WBC nuclei are not stained by exclusion.

The disclosed method also permits accurate WBC/Diff analysis in a blood sample that contains NRBC by subtracting signals identified as NRBC from the total WBC signals before WBC/Diff analysis is performed. Only one dye is needed for NRBC and damaged WBC staining. This enables the WBC/Diff analysis to be performed by the difference of light scattering characteristics of the WBC subclasses. WBC subclasses identified as damaged by FL3+ signals are added back to the subclass to they belong and thus producing an accurate WBC/Diff results in a sample containing damaged WBC's.

In the disclosed system, a vital stain is combined with a multipurpose reagent system which contains about 10 to 20 mM buffer, non-quaternary ammonium salt, a surfactant and a very low concentration of a WBC fixative, pH of about 6.0 to 7.5, osmolarity of about 230 to 310 mOsm/L, to carry out one step simultaneous analysis of WBC/Diff, NRBC, and damaged WBC.

Vital nucleic acid stains that can be used in the present invention must not permeate intact cell membrane and with relatively high extinction coefficient and low fluorescence intensity when they are not bound to nucleic acid. The spectral characteristics [Extinction (EX) max (nm)/Emission (EM) max (nm)] of the vital dyes must be compatible with the laser light source used in the system and their emission spectrum must not overlap that of the fluorochrome conjugated to the Mab used in immunophenotyping.

The following characteristics are desired for the vital stains for the disclosed system:

High extinction coefficient;
High quantum yield;
High binding affinity to nucleic acid;
Low fluorescence when it is not bound to nucleic acid; and
Spectral Characteristics must be compatible with the light source used in the detection system. e.g. For Argon laser light source, EX max around 488 nm and EM max around 630 nm.

This is not to limit the vital dyes with EX max range around 488 nm to be used with the disclosed methods. It will be obvious to those who are familiar in the art that the dyes with different EX max can be excited with appropriate light source such as HeNe, Xenon or Mercury lamps.

There number of nuclear dyes qualified for use in the disclosed system with appropriate light source. Some of the commercially available dyes that can be used in the disclosed system are 7-Aminoactinomycin D, YOYO-1, YOYO-3, TOTO-1, TOTO-3, BO-PRO-1, YO-PRO-1, TO-PRO-1, and many more.

In a preferred embodiment of the present invention, the qualified dyes which can be used with Argon laser which are also commercially available are Propidium iodide (PI), ethidium bromide (EBr), ethidium homodimer-1 (EthD-1), ethidium homodimer-2 (EthD-2), diethylene triamine (DTA).

In a preferred embodiment of the present invention, the vital stain is PI, the multipurpose reagent system has a pH of about 6.5 to 7.0, osmolarity of about 260, acetate buffer about 15 mM, ammonium chloride about 5.0 g/L, potassium bicarbonate about 2 g/L, saponin from about 100 mgs/L to about 150 mgs/L and formaldehyde about 0.07%, and a triple threshold signal qualification routine that qualifies signals for digitization using an AND/OR logic. Such a reagent is disclosed and described in PCT application Ser. No. WO94/18828, entitled "MULTIPURPOSE REAGENT SYSTEM FOR RAPID LYSIS OF WHOLE BLOOD SAMPLES", and herein incorporated by reference thereto. However, any lysing reagent can be utilized as long as the reagent does not damage the WBC cellular membranes so as to allow previously (pre-lysing) viable WBC nuclei to become stained.

The reagent/dye/sample mixture is then passed, essentially a cell at a time through an illuminated optical flow cell. This causes the cells to scatter the illuminating light and any stained nuclei present to fluoresce. The scattered and fluorescent light signals are detected by known means and, by using the triple triggering method in conjunction with the processing of the detected signals it is possible to identify and quantify WBC, WBC/Diff, damaged WBC and NRBC. A hematology analyzer which has been found to be particularly compatible with the triple trigger method of this invention is disclosed and described in U.S. application Ser. No. 08/283,379, entitled "METHOD AND APPARATUS FOR PERFORMING AUTOMATED ANALYSIS", filed on Jun. 7, 1995, and is herein incorporated by reference thereto. The following description is defined by this hematology analyzer. Such a description is merely for convenience and by no means is the present invention limited to only one instrument.

A portion of a whole blood sample, about 25 microliters, is deposited by means of a sample aspiration probe into the WBC cup which contains about 850 microliters of an isotonic lysing reagent. A lysing reagent is used to lyse the erythrocyte fraction of the blood sample and to lyse the cytoplasm of NRBC to expose the nuclei of any NRBC present. In addition to lysing the erythrocyte fraction of the blood, the reagent must be gentle enough to protect or not damage the WBC fraction. No matter what the formulation of the lyse utilized with the triple trigger method, the reagent will additionally contain, or be combined with, a small concentration of a vital nuclear stain which effectively labels any NRBC which might be present in the peripheral blood. Preferably, for use with the above referenced analyzer, the lysis chemistry will be configured such that the refractive index matches that of a sheath solution to substantially less than 0.1%.

The mixture of lyse reagent and sample will normally remain in the above referenced WBC cup only for 11 seconds. There it is lysed and mixed at 42° C.±3° C. At this point, the contents of the WBC cup are piped directly to an optical flowcell 100 for detection, see FIG. 1.

The measurement process begins as the cells stream passes through the flowcell 100, having been diluted with the addition of lyse so that the cells pass through the laser illuminated volume single file, in a laminar flowing sample stream surrounded by diluent/sheath solution. The illuminated volume is bounded in the two dimensions normal to the flow axis by the hydrodynamically focused cell stream, and in the dimension parallel to the flow axis by the vertical beam waist of the laser beam which is about 17 microns. When doing this test, the sample flow rate is about 2.5 microliters per second, and the corresponding illuminated sensing volume of the WBC and NRBC cells approximates an elliptical cylinder with dimension of about 80×5×17 microns. The 17 micron dimension is measured along the axis of the cylinder.

Figure 2:
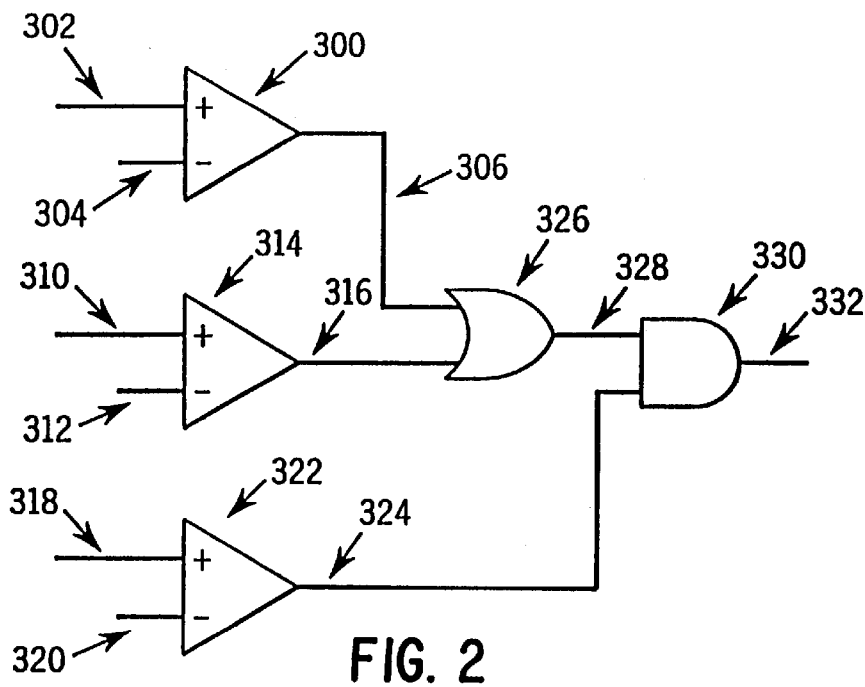
FIG. 2 is a diagram depicting a "Valid" triple trigger circuit.

At this point and as shown in FIG. 1, the presence of a cell is detected by a compound photodiode 102 detecting axial light loss (ALL) and intermediate angle scatter (IAS), photomultiplier tube 104 which detects red fluorescence, and a unique triple trigger circuit, shown in FIG. 2, in the three dimensional feature space of ALL, IAS, and FL3 (red fluorescence). The triple trigger circuit qualifies signals for digitization using AND/OR logic. A qualified signal must be greater than the IAS trigger, while at the same time it must be greater than either the ALL trigger or the FL3 trigger. The combination of this unique triggering circuit, and the lysing properties which include a balanced fixative, allow the exposed NRBC and damaged WBC nuclei to be rapidly stained, and clearly and non ambiguously counted and excluded from the WBC differential cell count without the usual interference from background, both fluorescent and non-fluorescent, such as DNA fragments, RBC stroma, and platelets.

One or more detectors are preferably placed in the forward light path for measuring forward intermediate angle scattering (IAS) and either small angle forward scattering (SAS) or axial light loss (ALL, also known as forward extinction). ALL is generally the decrease in light energy due to a cell passing in front of a laser beam and being detected by a photodiode. The light loss is generally due to scattering and defined as the decrease in light energy reaching a detector in the path of a laser beam due to the passage of a cell through that beam (generally ALL is detected at an angle of from about 0° to about 1°.) Small angle forward scatter (SAS), in contrast, is light energy that reaches a detector outside the incident laser beam (but within a narrow angle of from about 1° to 3°) due to scattering from a cell passing through the beam. A beam stop is generally provided to keep the laser beam from getting into the detector. ALL measuring systems collect light within the incident cone of laser illumination, while small angle scatter systems collect light outside this cone. In ALL measuring systems, the signal of interest is a negative signal subtracted from the steady state laser signal, whereas in small angle forward scatter measurement the signal is a small positive signal imposed on a very low background light level. Intermediate angle forward scattering (IAS) is similar to small angle forward scattering, except the light is scattered at a larger angle from the incident laser beam. More specifically, IAS relates to light scattered in a ring between about 3° and 10° away from the incident or center line of a laser beam. In a preferred embodiment, ALL is collected in the angles less than about 0.3° horizontally and less than about 1.20° vertically from the laser axis, and IAS is collected at angles between about 3° and 10° from the laser axis.

When cells, thus triggered, pass through the aforementioned illuminated volume, pulses are generated at detectors 102, 104, 106 and 108. The amplitudes of these pulses are then filtered, amplified, digitized, and stored in list mode in the corresponding five dimensional feature space of ALL, IAS, FL3, PSS (polarized side scatter) and DSS (depolarized side scatter). The normal counting time through flowcell 100 is 10 seconds. At the flow rate and dilution ratio described above, with a normal patient WBC count of 7000 cells per microliter of blood volume, the resulting event count rate would be 5000. In low count samples, this counting time can be automatically extended in order to improve the statistics of the measurement. At the conclusion of the measurement time, the sample stream is piped to waste, and probe is cleaned and dried and prepared to process a subsequent sample.

Algorithms are then applied to the list mode data of the aforementioned feature space of ALL, IAS, FL3, PSS, and DSS, and the following cell types are enumerated and/or flagged within less than 30 seconds of processing time:

| CELL TYPES ENUMERATED | PERCENTAGES | FLAGGED OR ENUMERATED |
|---|---|---|
| White Cell concentration | (WBC) | |
| Neutrophil concentration | % N of WBC | |
| Lymphocyte concentration | % LYMPH of WBC | |

-continued

| CELL TYPES ENUMERATED | PERCENTAGES | FLAGGED OR ENUMERATED |
|---|---|---|
| Monocyte concentration | % MONO of WBC | |
| Eosinophil concentration | % EOS of WBC | |
| Basophil concentration | % BASO of WBC | |
| NRBC | % NRBC of WBC | |
| Band concentration | | (BAND) |
| Blast concentration | | (BLST) |
| Immature gran. conc. | | (IG) |
| Variant-lymph conc. | | (VARL) |
| Damaged WBC | % WBC Damaged/ Count | |

ALL and IAS signals are detected and collected for the WBC/Diff analysis and FL3 signals from stained NRBC nuclei are collected for NRBC analysis, as will be described below. The triple trigger circuit, shown in FIG. 2, qualifies these signals for digitization using an AND/OR logic. To be qualified a signal must be greater than the IAS trigger, while at the same time it must be greater than either the ALL trigger or the FL3 trigger.

The various components and generated or utilized signals identified in FIG. 2 correspond to the following labels:

300—ALL Voltage Comparator
302—ALL Signal
304—ALL Threshold Voltage (Vth1)
306—ALL Voltage Comparator Output
310—FL3 Signal
312—FL3 Threshold Voltage (Vth2)
314—FL3 Voltage Comparator
316—FL3 Voltage Comparator Output
318—IAS Signal
320—IAS Threshold Voltage (Vth3)
322—IAS Voltage Comparator
324—IAS Voltage Comparator Output
326—OR Gate
328—OR Gate Output
330—AND Gate
332—Valid Trigger Output Real time signals from their respective channels are present at the inputs of the voltage comparators. Voltage comparators 300, 314 and 322 function by comparing the "+inputs" (302, 310 and 318) to the "−inputs" (304, 312 and 320) to resultant outputs (306, 316, 324). If the "+input" is of a higher voltage than the "−input" the output will be high. If the "+input" is of a lower voltage than the "−input" the output will be low.

The threshold voltages are independent voltages which are determined by system parameters.

The outputs of comparators 300 and 314 are inputs to OR gate 326 to give resultant OR gate output 328. The OR gate functions by comparing its inputs. The output will be high if either, or both, inputs are high.

The output of the OR gate 328 and the output of comparators 322 and 324 are inputs to AND gate 330. The AND gate functions by comparing its inputs to derive its output 332 which is also the valid trigger output. The output will be high only if both inputs are high.

The valid trigger output 332) will only be high if the IAS signal 318 is greater than its threshold voltage 320, and either or both, the ALL signal 302 is greater than its threshold voltage 304 or the FL3 signal 310 is greater than its threshold voltage 312.

ALL and IAS are collected for WBC/Diff analysis and Fluorescence (FL3) signals are collected for NRBC and damaged WBC analysis. A triple threshold circuit or qualification routine qualifies signals for digitization using AND/OR logic. According to this unique routine or circuit, to be qualified a signal must be greater than the IAS threshold, while at the same time it must be greater than either the ALL threshold or the FL3 threshold.

Figure 14A:
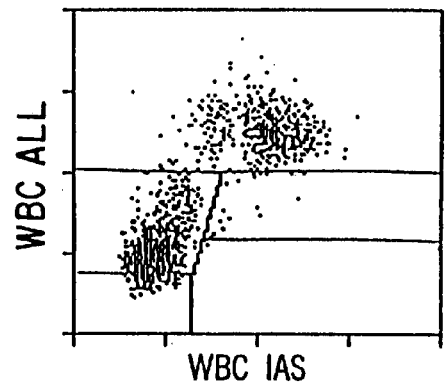
FIGS. 14A–14C depict the distributions of a whole blood sample which contained 56 NRBC/100 WBC utilizing the triple trigger (ALL, FL3 and IAS) detection method of the present invention.
Figure 14B:
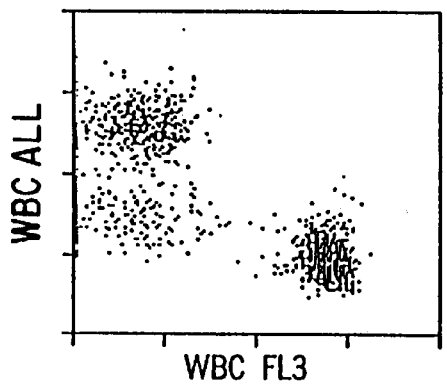
Figure 14C:
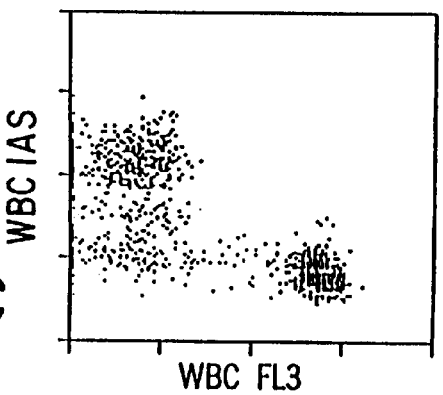

Using this triggering circuit, the NRBC's form a unique cluster in the aforementioned three dimensional space, see FIGS. 14 and 15, which can be easily counted during the Optical WBC Differential analysis, and exclude non ambiguously from the WBC count. Thus, a count of NRBC per 100 WBC, and a total NRBC per µL of patient blood is reported. Consequently, NRBC are subtracted from total WBC counts permitting accurate total WBC and Differential analysis in the presence of NRBC in a blood sample. The signals that are above both the ALL and FL3 triggers are identified as damaged WBC's. The damaged WBC subpopulation is identified in the same manner as in the intact WBC differential analysis. Background noise, both fluorescent and non-fluorescent, from DNA fragments, RBC stroma, platelets, Howell-Jolly Bodies, Basophilic Stippling, RNA from lysed reticulocytes and DNA from WBC and Megakaryocytic fragments are substantially eliminated. Stained NRBC nuclei are separated from the various background noise signals via the disclosed triple-triggering process (on ALL, IAS and FL3) and only the FL3+ signals from NRBC nuclei above the FL3 threshold on the ALL vs FL3 dot plot are counted as NRBC.

In FIGS. 3 through 10 the cell population areas identified by the below listed numbers, correspond to the following cell types:

| | |
|---|---|
| 202 = Lymphocytes | 208 = Origin Noise |
| 204 = Monocytes | 210 = NRBC |
| 206 = Granulocytes | 212 = Stroma |

Another technical advantage of the disclosed system is that it requires much lower concentration of the dye to effectively and rapidly stain NRBC for accurate detection and counting because of complete lysis of the cytoplasm of NRBC making their nuclei more accessible to the stain. This condition permits high signal to noise (S/N) ratio, greater than 100, in NRBC detection. The concentration of a vital dye required this system to rapidly perform the simultaneous analysis of WBC/Diff/NRBC/Damaged WBC is only 1 to 2 µg/ml which is at least 50 fold less than that in the previous art.

The disclosed method is unique in that simultaneous analysis of WBC/Diff/NRBC/Damaged WBC can be carried out automatically, accurately, and rapidly without interference from other cellular debris. Further advantage of the present invention is that it has a very high clinical value in that the method can be incorporated into a clinical hematology analyzer which routinely calibrate for WBC, RBC, and Platelet counts. Such a system is capable of producing an accurate WBC/Diff/NRBC/Damaged WBC data (% as well as absolute counts) in clinical blood samples. This has not previously been possible.

EXAMPLE 1

An EDTA-anti-coagulated fresh normal blood was run on an experimental unit of the automated clinical hematology analyzer described above and disclosed and described in U.S. application Ser. No. 08/283,379, entitled "METHOD AND APPARATUS FOR PERFORMING AUTOMATED ANALYSIS", filed on Jun. 7, 1995, and is herein incorporated by reference thereto. While the present invention was incorporated into the aforementioned analyzer it was not always utilized in all of the following examples. Twenty five (25) micro-liters of the blood sample were mixed on-line with 675 micro-liters of the isotonic multipurpose reagent (pH 6.5, 260 mosm/L) disclosed in PCT application Ser. No. WO94/18828, entitled "MULTIPURPOSE REAGENT SYSTEM FOR RAPID LYSIS OF WHOLE BLOOD SAMPLES", and herein incorporated by reference.

For the purposes of these experiments the multipurpose reagent system is comprised of about 95 mM ammonium chloride (5 g/l), about 0.075% by volume of formaldehyde, from about 10 mM to about 20 mM acetate buffer, about 10 mM potassium bicarbonate, and about 0.01% by weight volume (i.e., grams per 100 ml) of saponin. The pH of the reagent system is adjusted to a range of from about 6.2 to about 7.0 and the osmolality of the reagent system is from about 215 to about 270 mOsm/L.

The reagent is pre-warmed at 42° C.±3° in the instrument's heated mixing chamber, where the sample and reagent are mixed and incubated for 11 seconds. This mixture was then transported to the flow cell (which takes 8 and ½ seconds) for the WBC/Diff/NRBC analysis. The optical configuration of the system is presented in FIG. 1. The analysis was performed without implementing the triple triggering circuit; using only ALL and FL3 dual triggers as is common in the art. See all Figures from FIGS. 3A through 10C.

Figure 11A:
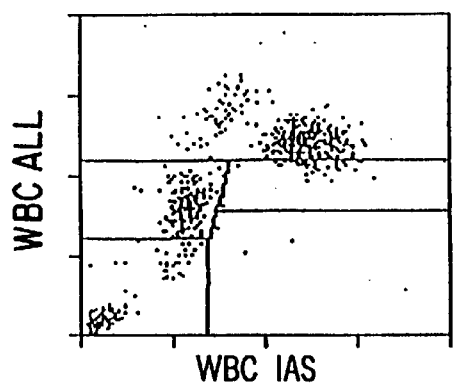
FIGS. 11A–11C show the dot plot displays of a normal blood sample processed as described in Example 1, utilizing normal or standard detection triggers.
Figure 11B:
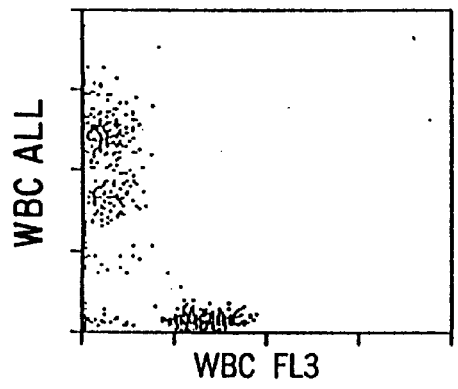
Figure 11C:
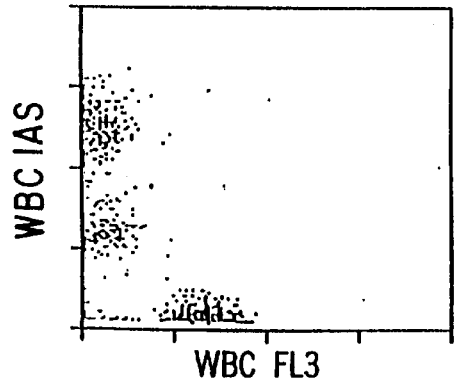

The upper dot plot display of FIG. 11A maps the light scatter signals (ALL vs. IAS) obtained from the sample and shows 3 distinct populations of WBC. The Basophil cluster is not apparent here because normal bloods do not contain many Basophils. The Eosinophil cluster is not shown here since Eosinophils are separated via a DSS vs. PSS dot plot (not shown) and the middle cytogram of FIG. 11B shows a dot plot display of ALL and FL3 signals as labeled. Note that normal blood does not contain any NRBCs. The lower bottom FL3+ clusters, FIGS. 11B and 11C, are apparently cell debris containing RNA or DNA, as described earlier.

EXAMPLE 2

Figure 12A:
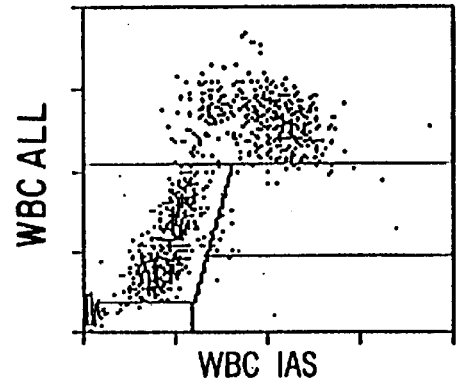
FIGS. 12A and 12B show the cytograms of an abnormal blood with NRBC, processed as described in Example 2, utilizing standard or normal detection triggers.
Figure 12B:
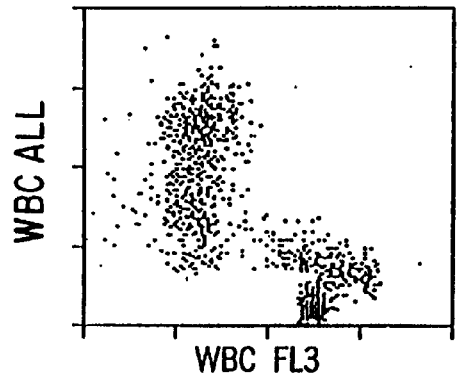

FIGS. 12A and 12B, top and bottom cytograms respectively, are dot plot displays of an abnormal blood with NRBC (47 NRBC/100 WBC) analyzed as described in Example 1 utilizing a standard detection method. The cluster right below the lymphocyte population in the top cytogram belongs to NRBC and the small cluster at the bottom, left corner belongs to the origin noise which include RBC stroma (reticula, Howell Jolly Bodies and etc.), platelets and WBC debris. FIG. 12B shows that the origin noise cluster of this sample stained with the nuclear dye brightly, following the stained NRBC cluster very closely in FL3 channel, thereby making it impossible to set the FL3 trigger to count NRBC accurately.

EXAMPLE 3

Figure 13A:
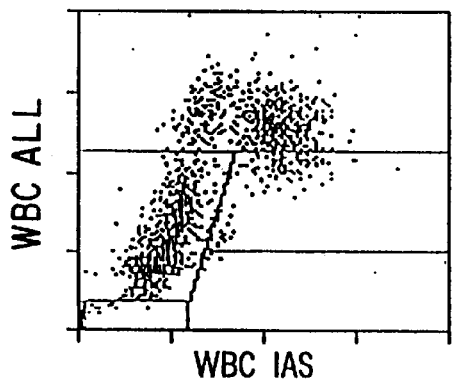
FIGS. 13A and 13B show the cytograms of an abnormal blood with NRBC, processed as described in Example 3, utilizing normal detection triggers.
Figure 13B:
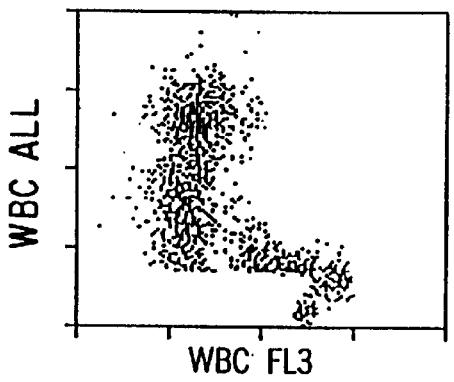

The cytograms for FIGS. 13A and 13B are dot plot displays of an abnormal blood with NRBC (51 NRBC/100 WBC) analyzed as described in Example 1 utilizing a standard detection method. The cluster right below the lymphocyte population in the top display, FIG. 13A belongs to NRBC. An increased FL3+ origin noise of this sample can be seen. The noise cluster is located very close to the NRBC cluster in the FL3 channel. Thus, the FL3 noise is interfering with the position of the FL3 trigger. When the FL3 trigger was set high enough to eliminate all the origin noise, a part of the NRBC population was also lost below the FL3 trigger as shown in FIG. 13B.

EXAMPLE 4

The disclosed triple trigger circuit (ALL/IAS/FL3), FIG. 2, of the present invention was incorporated into the same instrument used in EXAMPLES 1 through 3 and utilized during this procedure.

A EDTA, anti-coagulated clinical sample which contained 56 NRBC/100 WBC was processed as described in Example 1. The results are presented in FIGS. 14A through 14C. Note the disappearance of the FL3+ noise cluster. The noise signals are blocked by the added IAS trigger. The fluorescent origin noise from this abnormal blood is no longer visible above the FL3 trigger, although the trigger is set low enough to recover the total NRBC population. (Note the circular shape of the NRBC cluster.)

EXAMPLE 5

Figure 15A:
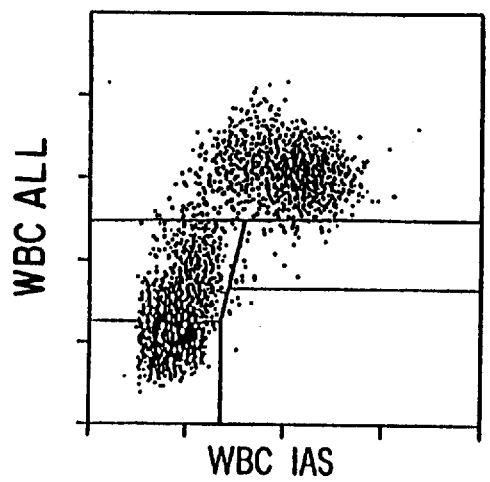
FIGS. 15A and 15B depict the distributions of another whole blood sample which contained 140 NRBC/100 WBC, also utilizing the triple trigger (ALL, FL3 and IAS) detection method of the present invention.
Figure 15B:
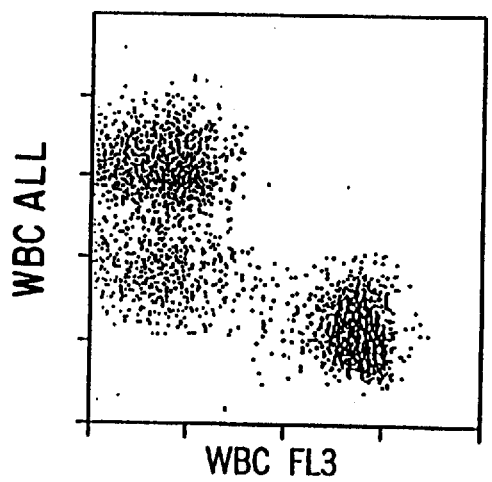

FIGS. 15A and 15B show the dot plot displays of the NRBC distribution of another clinical whole blood sample which contained 140 NRBC/100 WBC, also post triple trigger (ALL, FL3 and IAS) implementation. The origin noise is not visible and the total NRBC population is recovered above the FL3 trigger. Note the heavy density of the NRBC cluster due to the very high concentration of NRBC in this sample.

EXAMPLE 6

Figure 16A:
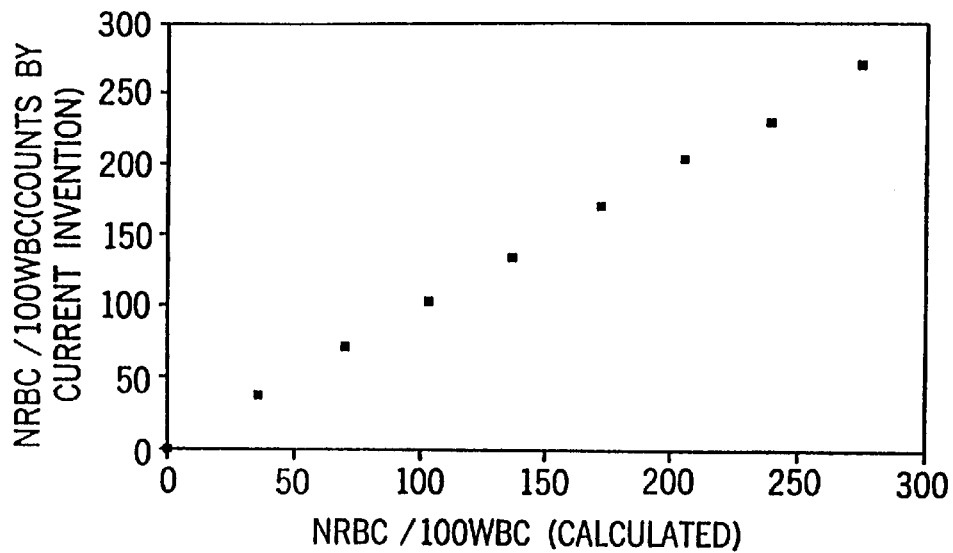
FIGS. 16A and 16B show the results of linearity samples that were prepared and processed as described in Example 6 by utilizing a method of the present invention.
Figure 16B:
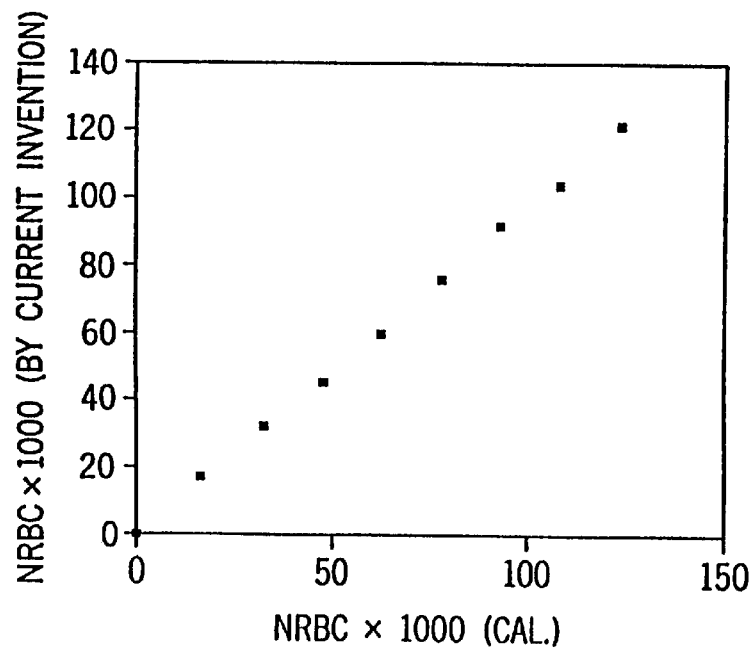

Linearity samples were prepared by adding various concentrations of unfixed chicken erythrocytes to a EDTA, anti-coagulated normal human blood. The samples were processed as described in Example 1 utilizing the triple trigger detection method of the present invention. The cytoplasm of chicken erythrocytes lyse in the method of present invention leaving only naked nuclei (CEN). The CEN stained very rapidly with the vital nuclear stain (PI) in the diluent and become fluorescent (FL3). The FL3+ CEN are counted as NRBC and reported as number of NRBC/100 WBC and as absolute counts per $\mu$L of the whole blood sample in the method of the present invention. The results are presented in FIGS. 16A and 16B. The linearity plots of NRBC/100 WBC and NRBC in absolute numbers in the figure demonstrate that the method of the current invention generate a linear NRBC counts.

EXAMPLE 7

Figure 17:
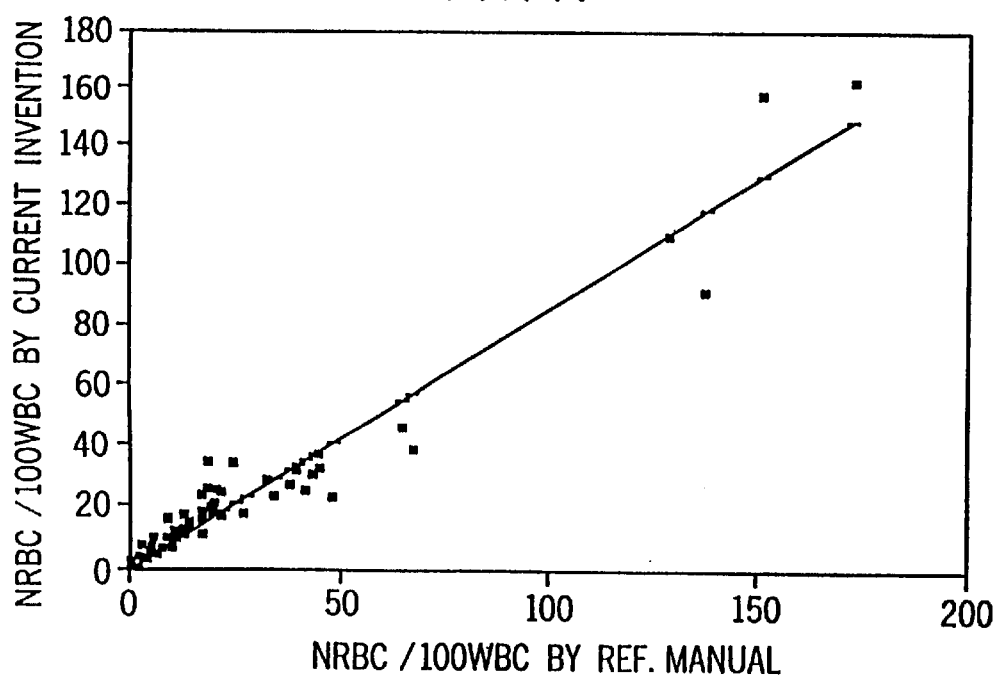
FIG. 17 is the correlation plot of an automated hematology analyzer's NRBC counts (ordinate) utilizing a method of the present invention and manual microscopic NRBC counts (abscissa). The data were processed as described in Example 7.
Figure 3A:
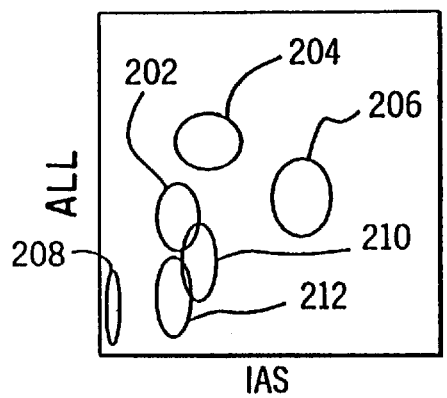
FIGS. 3A, 3B and 3C are drawings of the WBC, NRBC, RBC stroma and other background noise distribution of a whole blood sample processed as described in Example 1, utilizing standard or normal detection triggers.
Figure 4A:
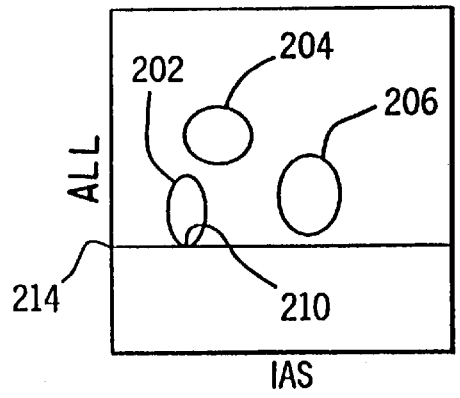
FIGS. 4A, 4B and 4C are drawings of the WBC, NRBC, RBC stroma and other background noise distribution of a whole blood sample processed as described in Example 1 utilizing only an 0° to about 1° scatter axial light loss (ALL) trigger.
Figure 3B:
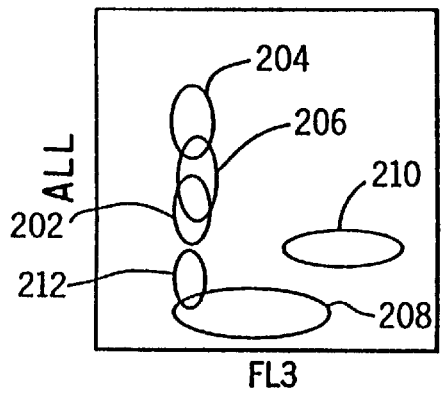
Figure 4B:
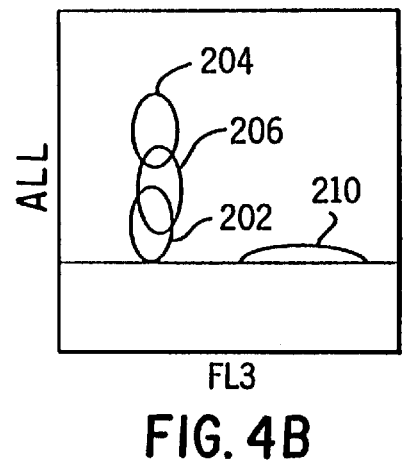
Figure 3C:
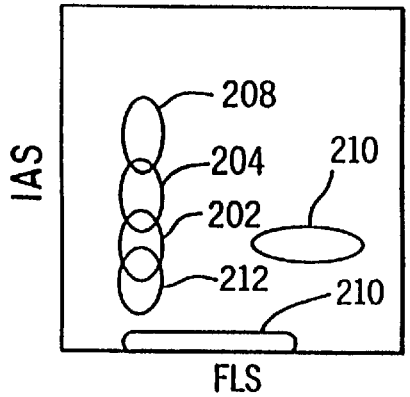
Figure 4C:
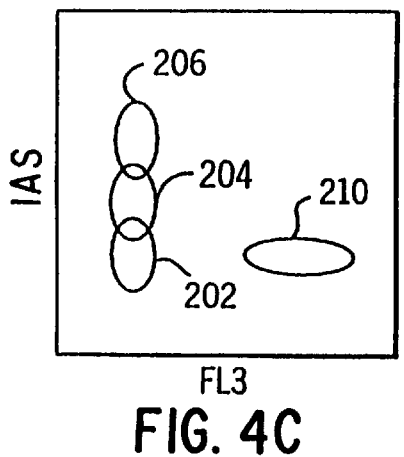
Figure 5A:
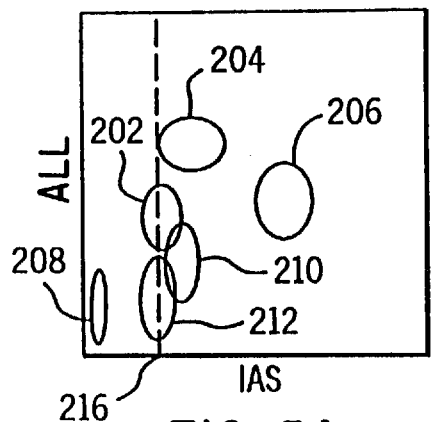
FIGS. 5A, 5B, and 5C are drawings of the WBC, NRBC, RBC stroma and other background noise distribution of a whole blood sample processed as described in Example 1 utilizing only a 3°–10° intermediate angle scatter (IAS) trigger.
Figure 6A:
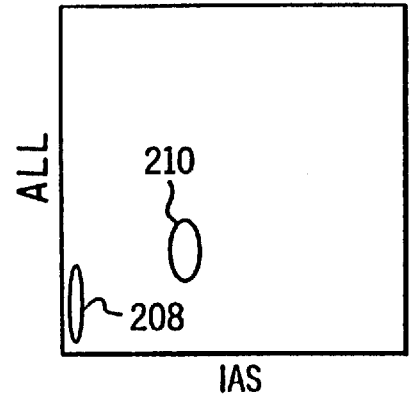
FIGS. 6A, 6B and 6C are drawings of the NRBC, RBC stroma and other background noise distribution of a whole blood sample processed as described in Example 1 utilizing only a fluorescence (FL3) trigger.
Figure 5B:
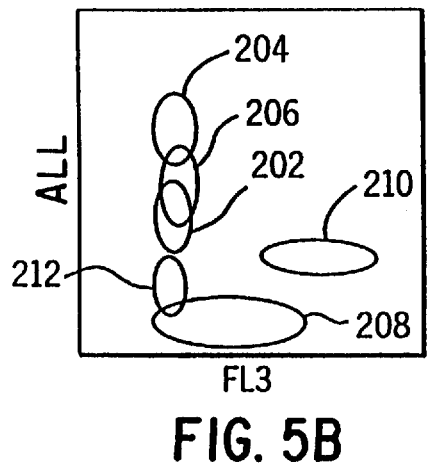
Figure 6B:
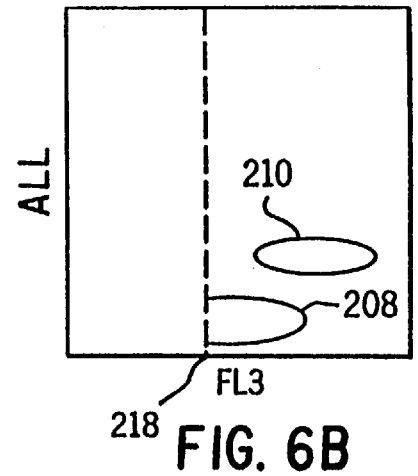
Figure 5C:
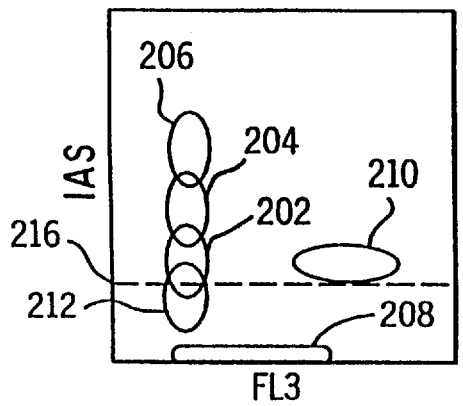
Figure 6C:
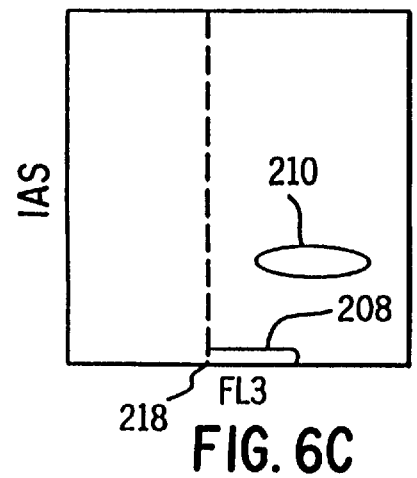
Figure 7A:
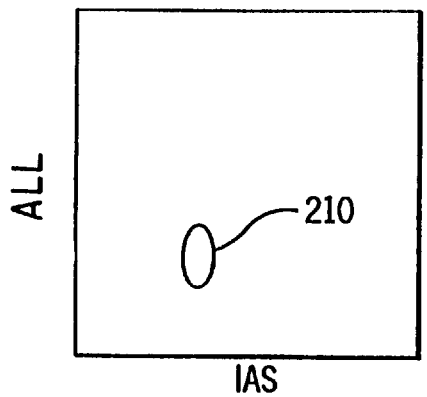
FIGS. 7A, 7B and 7C are drawings of the NRBC distribution of a whole blood sample processed as described in Example 1 utilizing a trigger level for FL3 higher than for the trigger utilized in FIG. 6 to eliminate the noise signals.
Figure 8A:
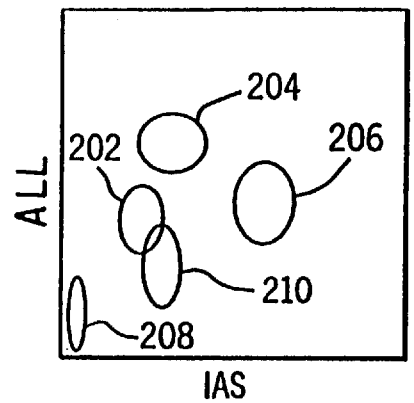
FIG. 8 is a drawing of the WBC, NRBC and other background noise distribution of a whole blood sample processed as described in Example 1 utilizing two triggers, ALL and FL3, electronically "OR'ed" together.
Figure 7B:
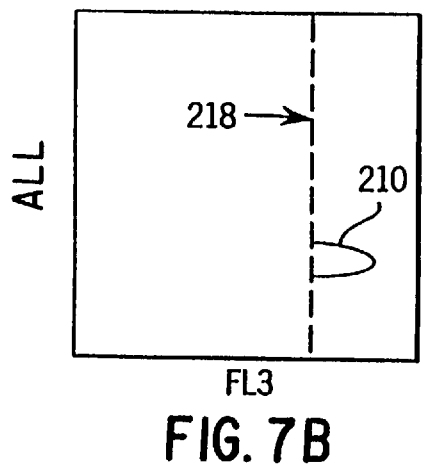
Figure 8B:
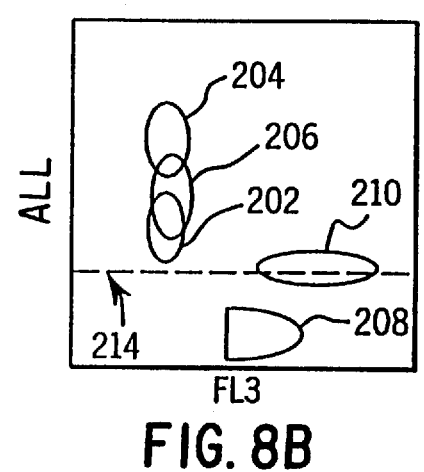
Figure 7C:
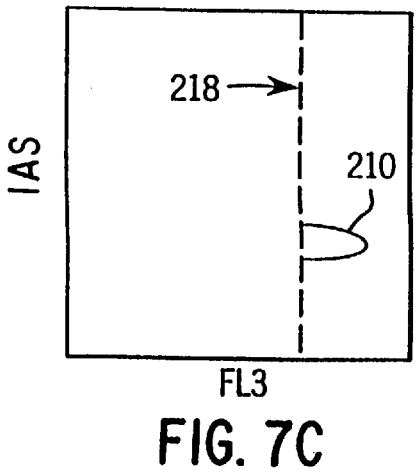
Figure 8C:
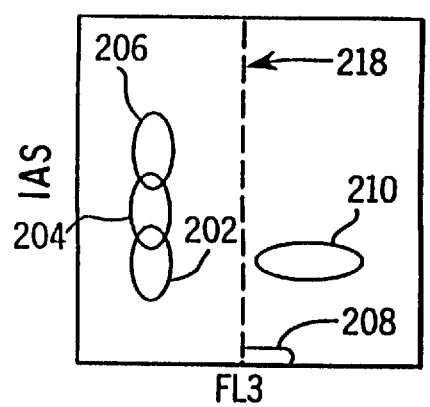
Figure 9A:
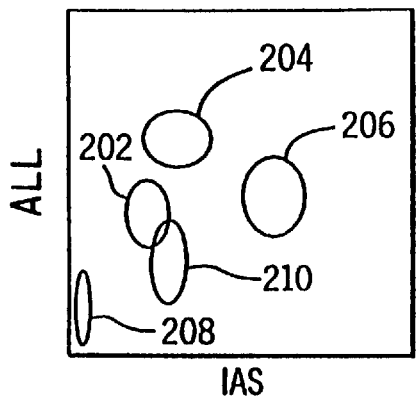
FIGS. 9A, 9B and 9C are drawings of the WBC and NRBC distribution of a whole blood sample processed as described in Example 1, utilizing two triggers ALL and FL3 electronically "OR'ed" together with the level of FL3 trigger set at a higher value than in FIG. 8.
Figure 10A:
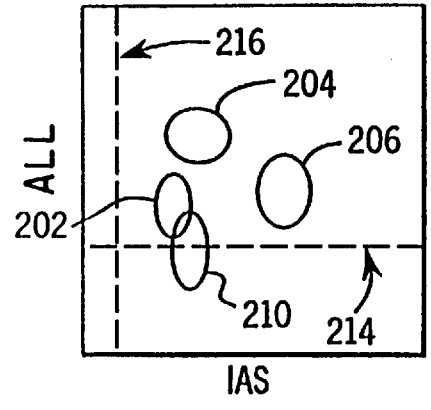
FIGS. 10A, 10B and 10C are drawings of the WBC and NRBC distribution of a whole blood sample processed as described in Example 1, with triggers for ALL, IAS and FL3.
Figure 9B:
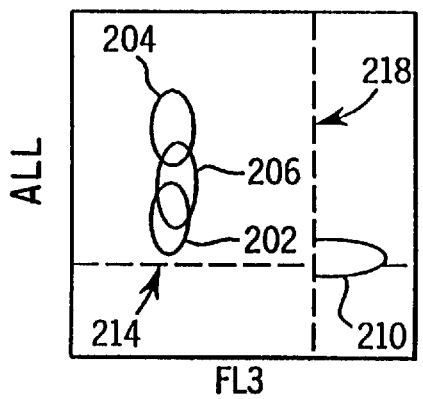
Figure 10B:
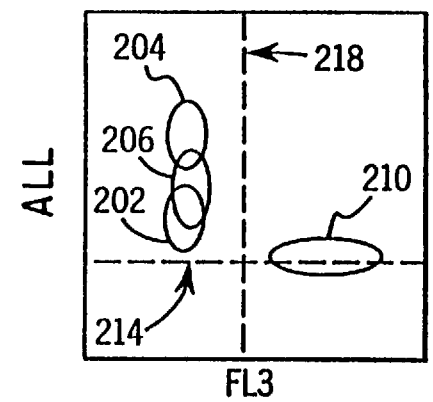
Figure 9C:
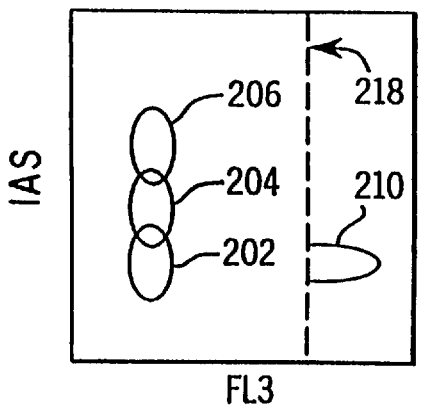
Figure 10C:
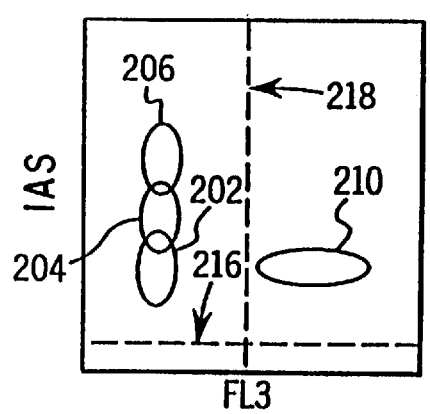

FIG. 17 shows the correlation plot of NRBC counts (ordinate) of 85 clinical samples obtained by the method of the current invention. The results were correlated to that of reference manual microscopic counts (abscissa). For manual NRBC counts, 200 cell WBC differential was performed on each patients' blood smears stained with Wright-Giemsa and NRBC counts present in the same region were divided by 2 to report NRBC/100 WBC. Correlation coefficient (R) is 0.973 (R2=0.946), the slope is 0.86 and Y-intercept is 1.32.

EXAMPLE 8

Figure 18A:
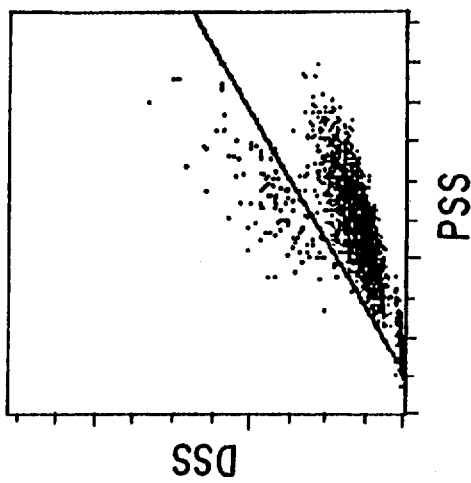
FIGS. 18A–18F show the cytograms of a normal blood sample as described in Example 8.
Figure 18C:
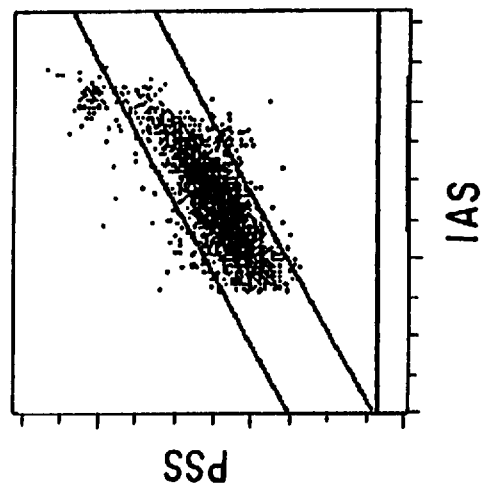
Figure 18B:
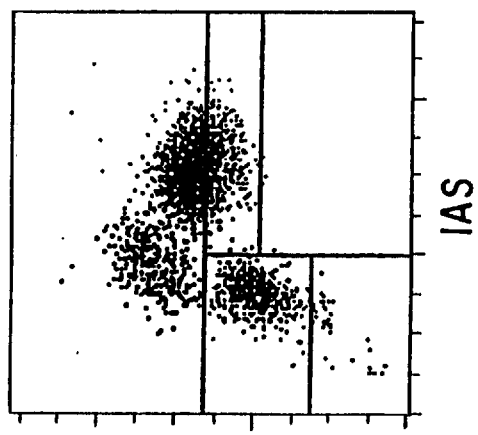
Figure 18D:
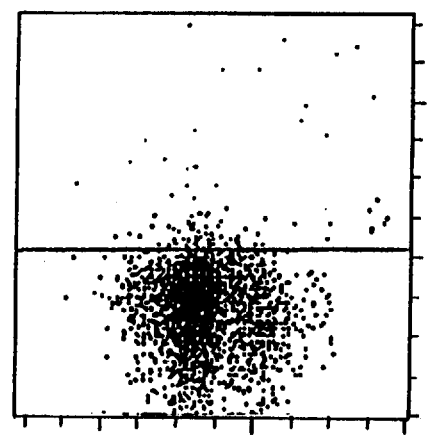
Figure 18F:
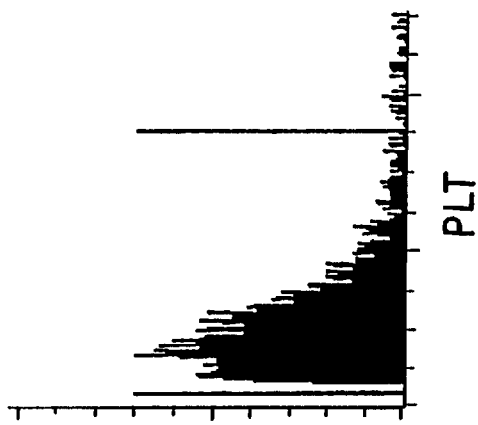
Figure 18E:
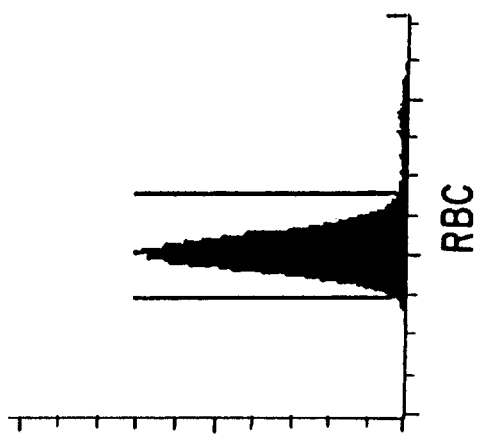

Twenty five (25) micro-liters of the blood sample was mixed and incubated on-line at 42° C. for 11 seconds with 675 micro-liters of the multipurpose reagent of Example 1 (pH 7.0, 260 mOsm/L) in to the heated vortexer of the hematology analyzer disclosed and described in U.S. application Ser. No. 08/283,379, entitled "METHOD AND APPARATUS FOR PERFORMING AUTOMATED ANALYSIS", filed on Jun. 7, 1995. This mixture was then automatically transported to the flow cell and analyzed (approximately 8 and ½ seconds for WBC/Diff/NRBC analysis.) FIGS. 18A–18F are the cytograms of the blood. The top left cytogram, FIG. 18A, of the light scatter signals (ALL vs IAS) shows 3 distinct populations of WBC (neutrophils, monocytes and lymphocytes. Basophil cluster is not apparent here because a normal blood contains only about 1% or less basophils. Eosinophils are separated on the top right DSS vs PSS cytogram, FIG. 18B. The middle left cytogram, FIG. 18C, is a display of ALL and FL3 signals. Note that normal blood does not contain any NRBC and that there are only few damaged cells to the right of the vertical line in FIG. 18C (FL3+ signals).

EXAMPLE 9

An abnormal blood with NRBC ( 4.99k/$\mu$L or 46.6 NRBC/100 WBC) was analyzed as described in Example 8 and the results are presented in FIGS. 19A–19F. The cluster right below the lymphocyte population in the top left cytogram (ALL vs IAS), FIG. 19A, belongs to NRBC. The bottom right cytogram (ALL vs FL3+), FIG. 19F, reveals that the stripped NRBC nuclei are stained brightly and pulled above the FL3+ trigger and counted. The NRBC counts are then subtracted from the total WBC counts before WBC differential analysis, producing an accurate WBC/Diff results.

EXAMPLE 10

Figure 20A:
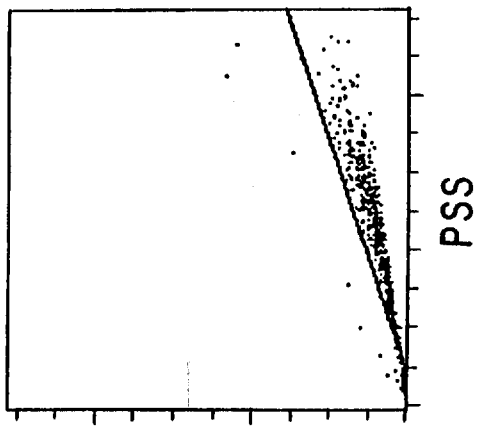
FIGS. 20A–20F show cytograms of a sample containing damaged lymphocytes as described in Example 10.
Figure 20B:
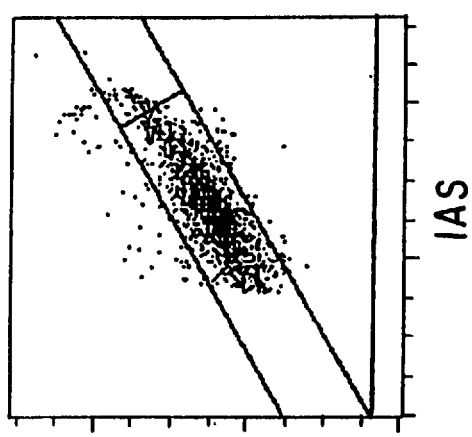
Figure 20C:
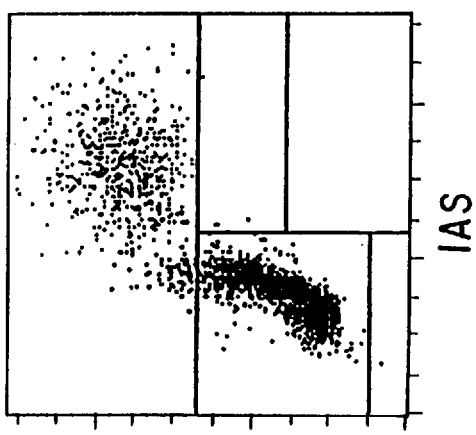
Figure 20D:
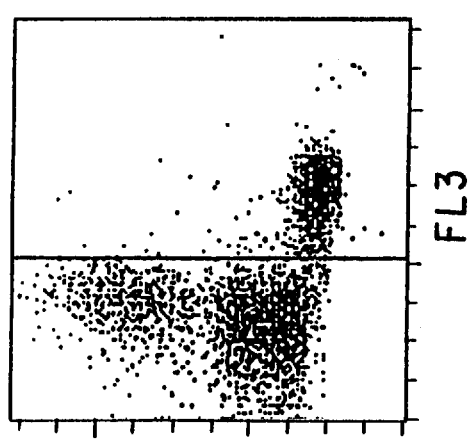
Figure 20F:
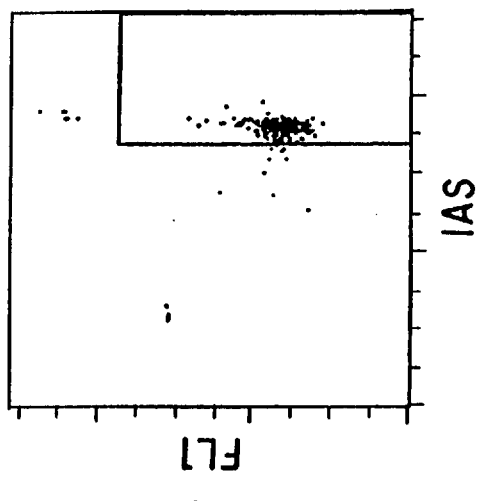
Figure 21B:
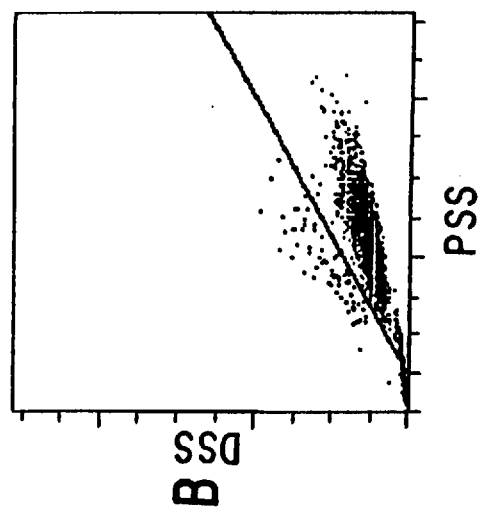
FIGS. 21A–21F show cytograms of a normal blood aged 35 hrs under refrigeration as described in Example 11.
Figure 20E:
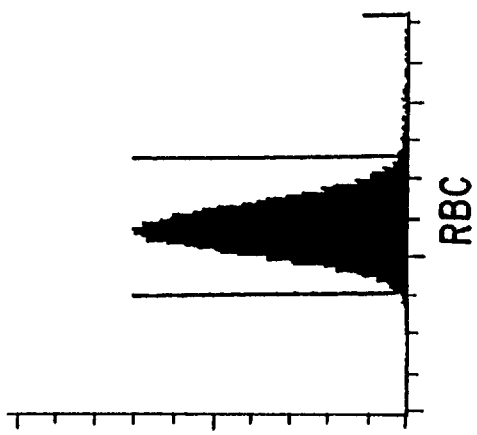
Figure 21A:
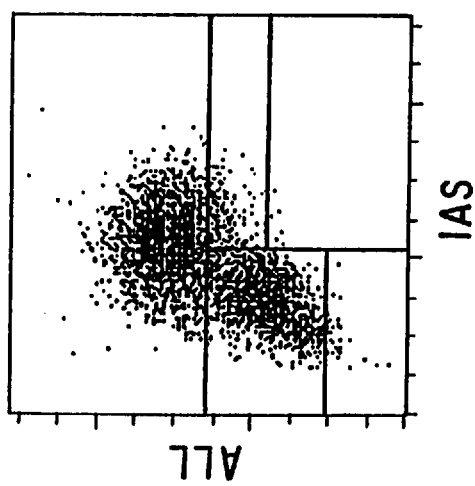
Figure 21C:
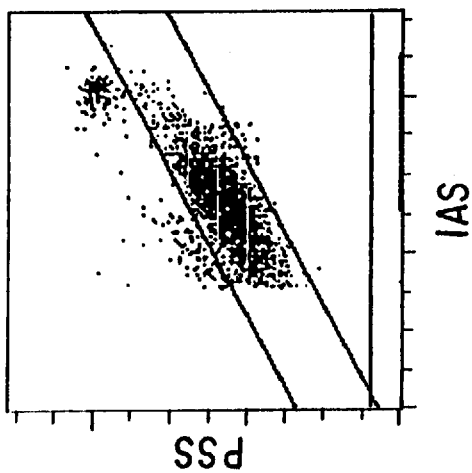
Figure 21D:
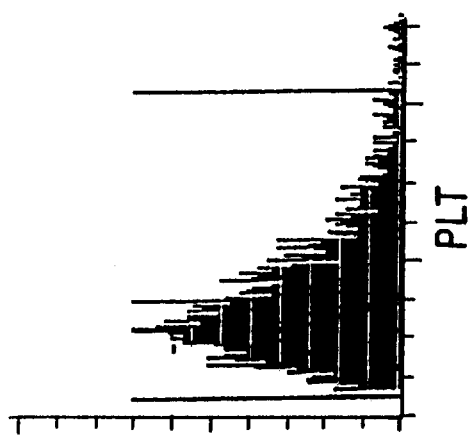
Figure 21E:
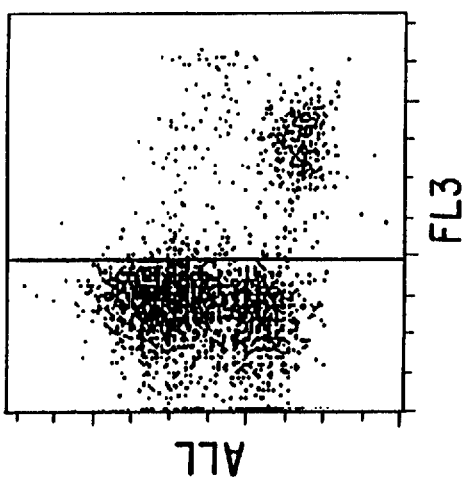
Figure 21F:
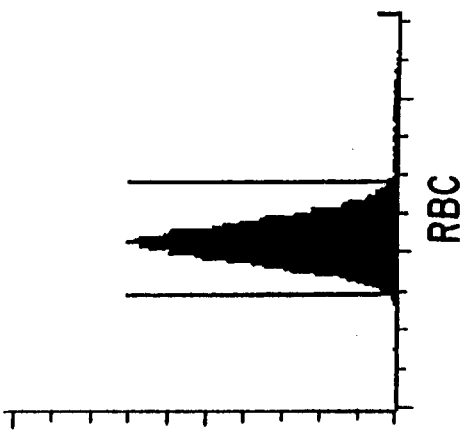

A clinical sample (CLL) which contains damaged lymphocytes was analyzed as described in Example 8 and the results are presented in FIGS. 20A–20F. The cluster to the immediate lower right of the lymphocyte population in the top cytogram (ALL vs IAS), FIG. 20A, belongs to damaged lymphocytes. FIG. 20C (ALL vs FL3+) shows that almost one-half of the lymphocyte population stained with the nucleic acid dye (PI). Microscopic smear review of the sample revealed that about 50% of the lymphocyte population was either smudged or had lost their cytoplasmic membrane (naked nuclei). The damaged lymphocytes are distinguished from NRBC's along the ALL axis since their light scatter signals are higher than that of the stripped NRBC nuclei.

EXAMPLE 11

Figure 19B:
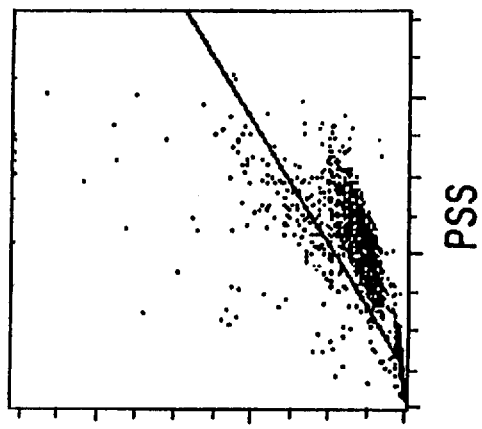
FIGS. 19A–19F show the cytograms of an abnormal blood sample with NRBC (4.99 k/$\mu$L or 46.6 NRBC/100 WBC) and as described in Example 9.
Figure 19A:
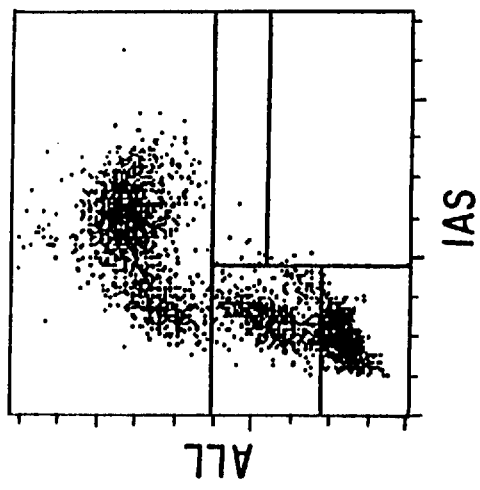
Figure 19C:
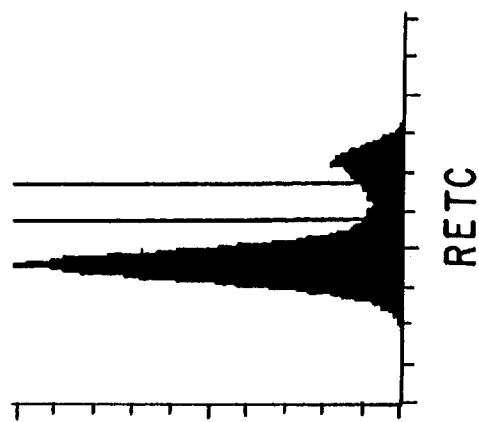
Figure 19D:
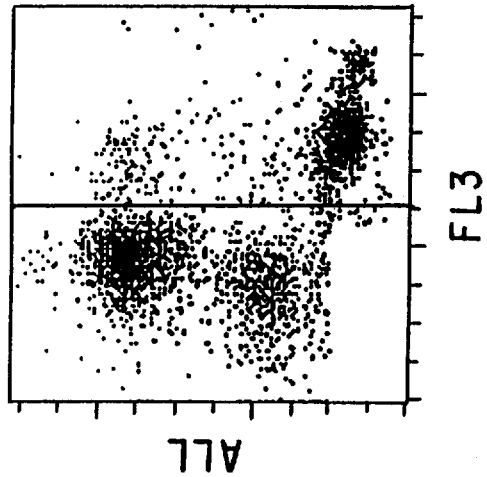
Figure 19E:
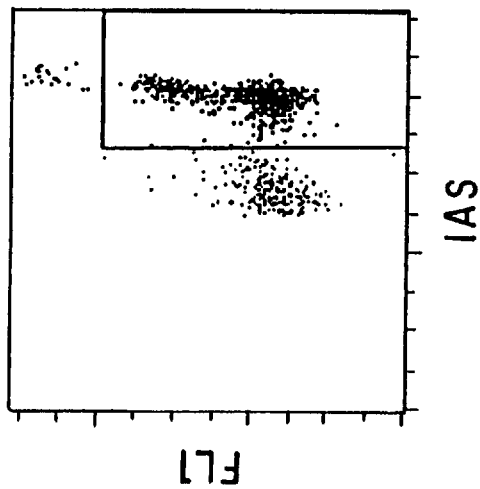
Figure 19F:
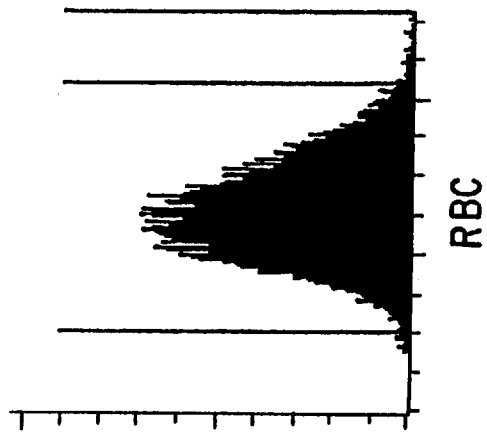

A normal blood sample aged for 35 hours under refrigeration was analyzed as described in Example 8 and the results are presented in FIGS. 21A–21F. The sample was processed as described in Example 8. The FL3+ signals shown on the ALL vs FL3 cytogram to the right of granulocytes and lymphocytes, FIG. 19F, represent damaged granulocytes and lymphocytes respectively.

EXAMPLE 12

Figure 22A:
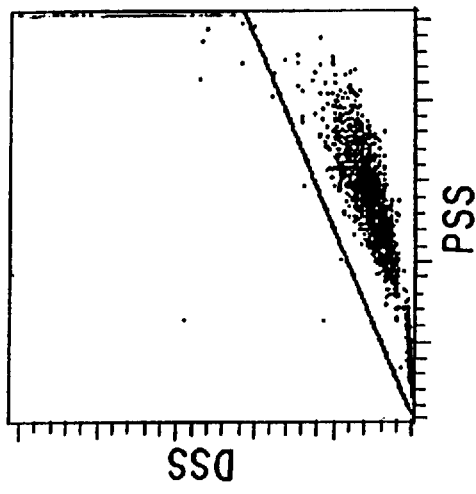
FIGS. 22A–22F show cytograms of a manipulated sample in which hard-fixed human WBC's and platelets are mixed with human RBC fraction and re-suspended in a human plasma as described in Example 12.
Figure 22B:
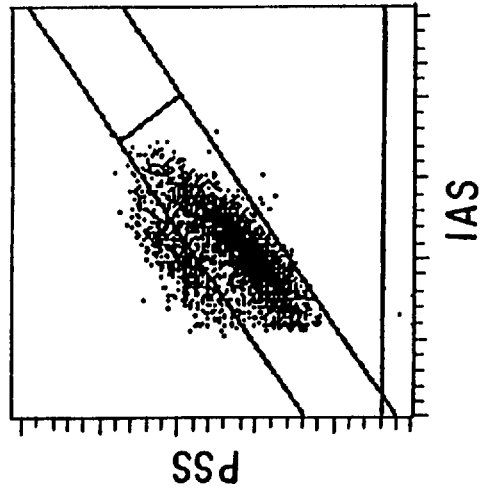
Figure 22C:
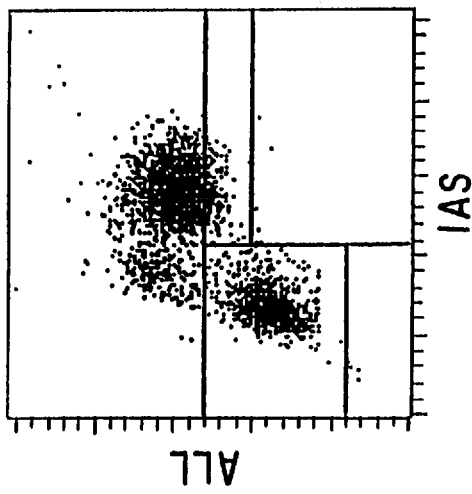
Figure 22D:
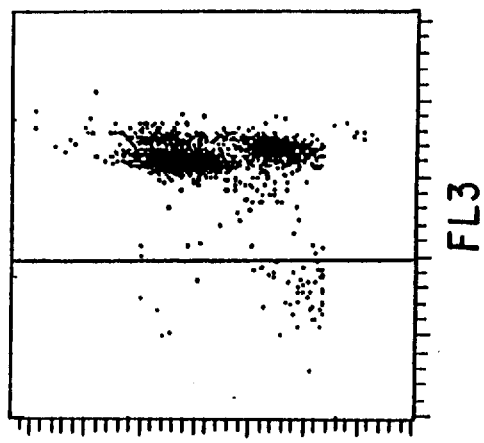
Figure 22F:
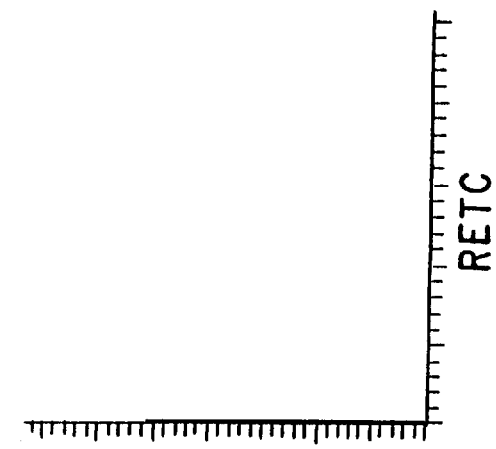
Figure 22E:
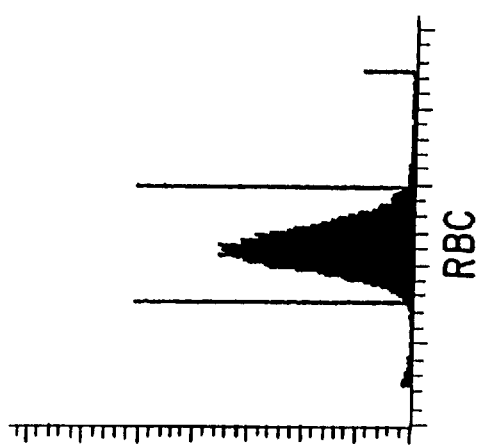

A manipulated sample in which hard-fixed human WBC's and platelets were mixed with human RBC fraction and re-suspended in a human plasma. This mixture was analyzed as in Example 8 and the results are presented in FIGS. 22A–22F. Unlike WBC's preserved by the multi-purpose reagent system disclosed herein, the ALL vs FL3 cytogram, FIG. 22C, of the hard-fixed cells reveal that all the WBC's are intensely stained. The cross-linking reagent makes the cell membrane very porous permitting the nucleic acid dye to penetrate into the cells. Subpopulations of WBC's are identified via multi-dimensional light scatter analysis as described in U.S. application Ser. No. 08/283,379, entitled "METHOD AND APPARATUS FOR PERFORMING AUTOMATED ANALYSIS", filed on Jun. 7, 1995.

EXAMPLE 13

Figure 23B:
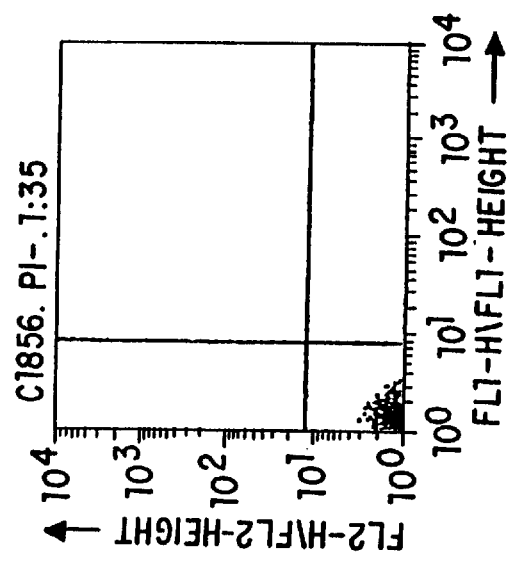
FIGS. 23A–23F are commercial flow cytometer displays of a blood sample processed as described in Example 13.
Figure 23A:
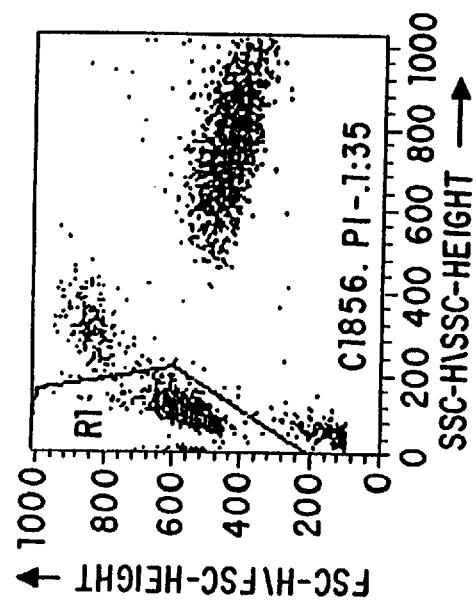
Figure 23D:
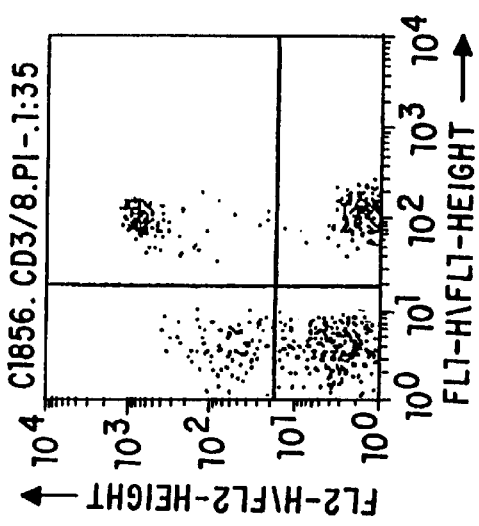
Figure 23F:
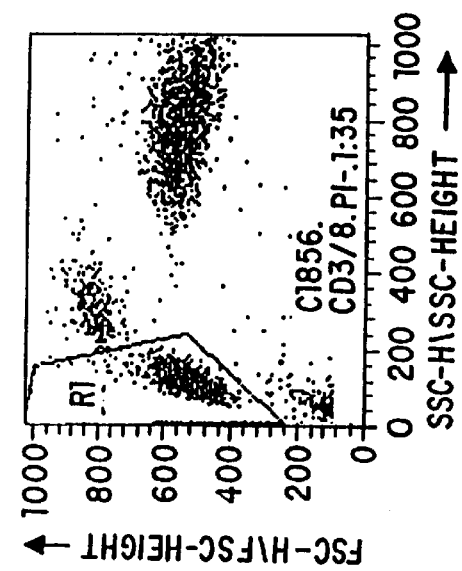
Figure 23C:
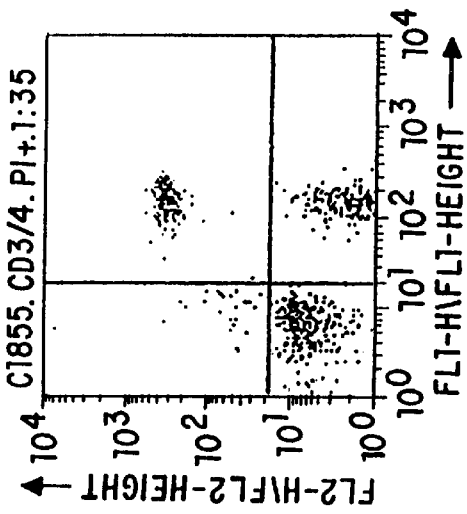
Figure 23E:
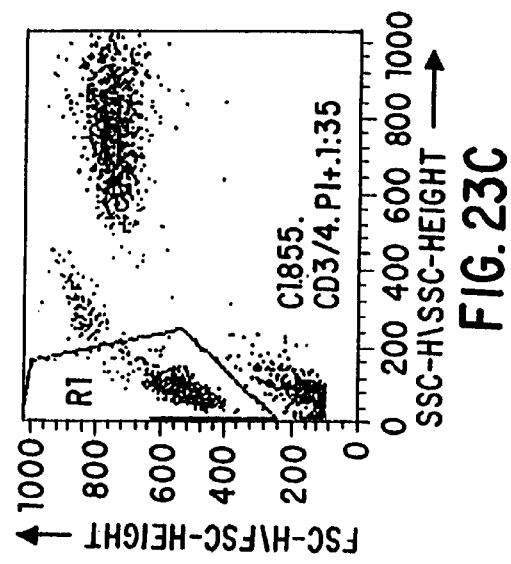

Fifty $\mu$L each of two normal blood samples were mixed with 10 $\mu$L of Mab solution containing anti-CD3FITC and anti-CD4-PE in separate test tubes. A second 50 $\mu$L aliquot of the normal blood samples were mixed with 10 $\mu$L of Mab solution containing anti-CD3FITC and anti-CD8-PE in two additional and separate test tubes. A negative control was prepared without adding any Mab to a test tube. The mixtures were incubated at room temperature for 15 min before adding 1.7 ml of the multipurpose reagent of Example 1 without any nucleic acid dye, prewarmed at 42° C. to each tube. The samples were presented to a FACScan® instrument (Becton, Dickinson & Co.) and the signal acquisition was begun exactly at 11 seconds after the addition of the multipurpose reagent. The results are presented in FIGS. 23A–23F, and Table 1. The top cytograms, FIGS. 23A & B represent the negative control of the normal blood, the left cytogram, FIG. 23A shows forward scatter (FCS) vs 90° side scatter showing the lymphocyte gating; the right cytogram, FIG. 23B shows the two dimensional display of FL1 vs FL2; the middle cytograms, FIGS. 23C & D represent the same sample but reacted with anti-CD4 Mab; the bottom cytograms, FIGS. 23E & F represent the same blood but reacted with anti-CD8 Mab.

EXAMPLE 14

Figure 24B:
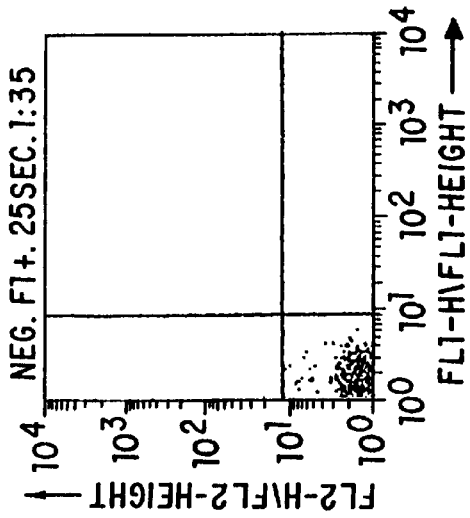
FIGS. 24A–24F are commercial flow cytometer displays of a blood sample processed as described in Example 14.
Figure 24D:
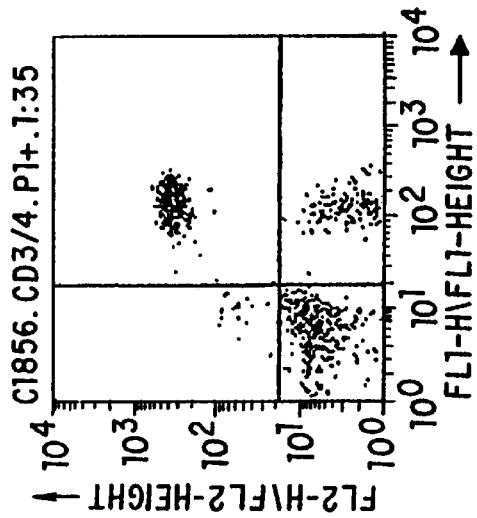
Figure 24A:
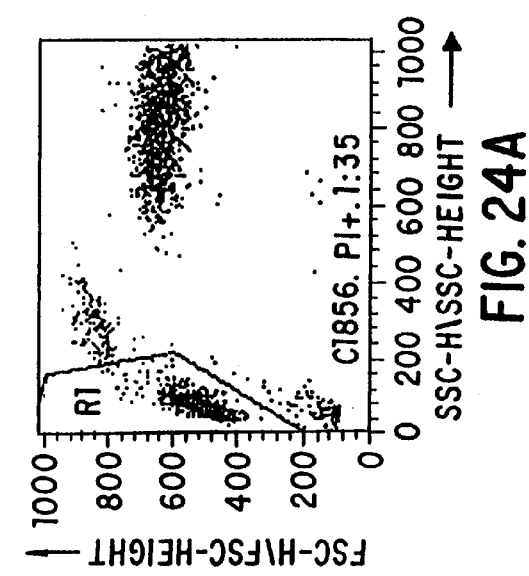
Figure 24C:
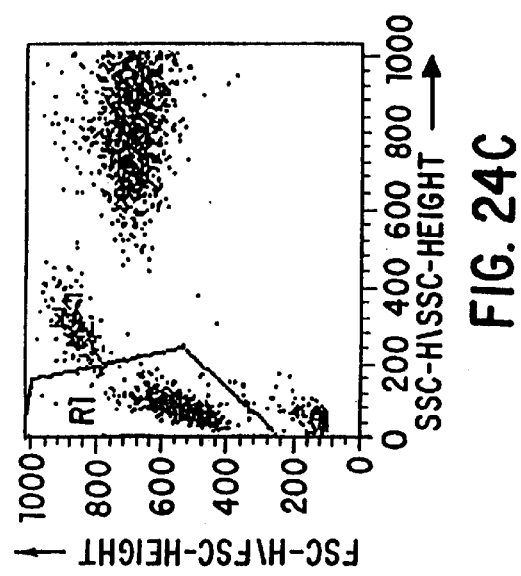
Figure 24F:
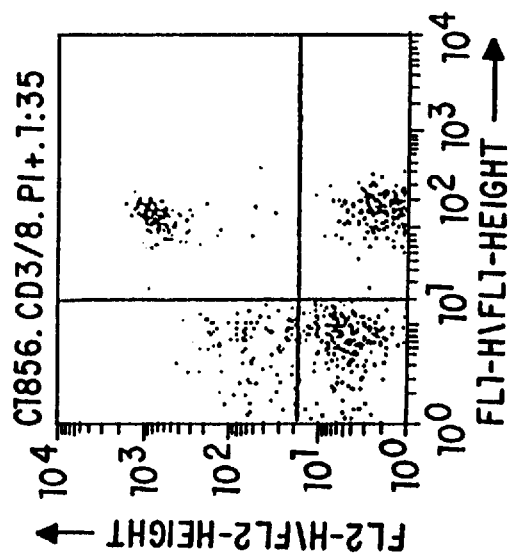
Figure 24E:
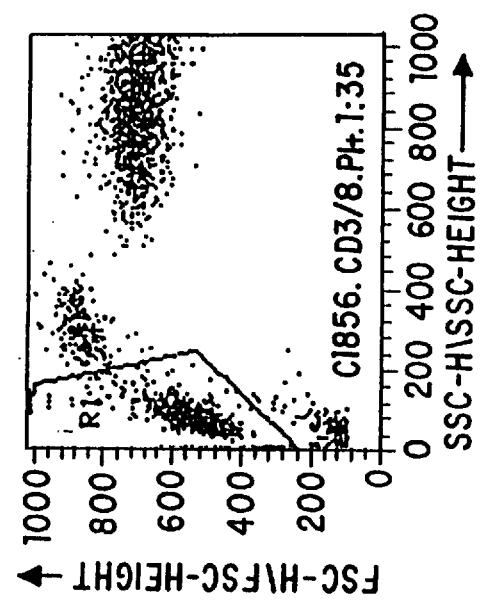

Fifty $\mu$L of two normal blood samples were mixed with 10 $\mu$L of Mab solution containing anti-CD3FITC and anti-CD4-PE in a test tube. To a second tube, 50 $\mu$L of a normal blood sample was mixed with 10 $\mu$L of Mab solution containing anti-CD3FITC and anti-CD8-PE in a test tube. A negative control was prepared without adding any Mab. The mixture was incubated at room temperature for 15 min before adding 1.7 ml of the multipurpose reagent described above with PI (0.2 $\mu$g/ml), prewarmed at 42° C. The sample were presented to a FACScan® instrument (Becton, Dickinson & Co.) and the signal acquisition was begun exactly at 11 seconds after the addition of the multipurpose reagent. The results are presented in FIGS. 24A–24F and Table 1. The top cytograms, FIGS. 24A & B, represent a negative control of a normal blood, the left cytogram, FIG. 24A shows forward scatter (FCS) vs 90° side scatter showing the lymphocyte gating; the right cytogram, FIG. 24B, is the two dimensional display of FL1 vs FL2; the middle cytograms, FIGS. 24C & D, represent the same sample but reacted with anti-CD4 Mab; and the bottom cytograms, FIGS. 24E & F, represent the same blood but reacted with anti-CD8 Mab.

TABLE 1

| Sample ID | Quadrant Position | Without PI (% Gated) | With PI (% Gated) |
| --- | --- | --- | --- |
| Neg Control | UL | 0.00 | 0.00 |
| C1855 | UR | 0.00 | 0.00 |
|  | LL | 100.00 | 100.00 |
|  | LR | 0.00 | 0.00 |
| CD3FITC/CD4PE | UL | 2.20 | 2.96 |
| C1855 | UR (Helper T) | 24.62 | 26.65 |
|  | LL | 34.73 | 33.94 |
|  | LR | 38.46 | 36.45 |

TABLE 1-continued

| Sample ID | Quardrant Position | Without PI (% Gated) | With PI (% Gated) |
|---|---|---|---|
| CD3FITC/CD8PE | UL | 3.16 | 3.34 |
| C1855 | UR (Suppressor T) | 34.12 | 32.09 |
|  | LL | 33.11 | 32.73 |
|  | LR | 29.60 | 31.84 |
| Neg Control | UL | 0.00 | 0.11 |
| C1856 | UR | 0.00 | 0.00 |
|  | LL | 100.00 | 99.89 |
|  | LR | 0.00 | 0.00 |
| CD3FITC/CD4PE | UL | 0.97 | 1.68 |
| C1856 | UR (Helper T) | 47.85 | 44.47 |
|  | LL | 32.72 | 35.54 |
|  | LR | 18.47 | 18.30 |
| CD3FITC/CD8PE | UL | 8.31 | 9.29 |
| C1856 | UR (Suppressor T) | 15.61 | 16.98 |
|  | LL | 27.65 | 26.64 |
|  | LR | 48.43 | 47.09 |

What is claimed is:

1. A method of differentiating nucleated red blood cells (NRBC), damaged white blood cells (WBC) and WBC in a sample by flow cytometry comprising:

(a) adding fluorescently labeled antibodies to an aliquot of a blood sample, incubating the antibody/sample, and mixing for a time sufficient for the antibodies to bind with their surface antigen binding partner;

(b) further mixing the aliquot with a reagent system which comprises a red blood cell (RBC) lysing component and a vital nuclear stain component to stain the nuclei of NRBC and any damaged WBC, wherein the lysing component lyses RBC while minimizing damage to WBC cellular membranes;

(c) passing the mixed aliquot, substantially a cell at a time, through an area of optical stimulation;

(d) obtaining at least one signal for the Parameter of fluorescence (FL) and at least one signal for the parameter of scattered light at both a first and second range of scatter angle;

(e) qualifying the signals obtained by subjecting the signals to a logic wherein a signal to be qualified must be greater than a second scatter signal threshold, while at the same time the signal must be greater than either a first scatter signal threshold or a FL threshold wherein the thresholds are set to eliminate spurious FL noise signals and include NRBC population signals in the signals obtained;

(f) constructing a three dimensional plot of intensity signals of FL and scattered light from the obtained and qualified signals; and (g) differentiating WBC, NRBC, and damaged WBC by a WBC sub-class differential (WBC/Diff) from the constructed three-dimensional plot and the qualified signals and determining the number of cells of each class and sub-class, wherein the determined NRBC is subtracted from the determined WBC counts before differentiating the WBC/Diff.

2. A method of differentiating nucleated red blood cells (NRBC), damaged white blood cells (WBC), WBC and a WBC subclass differential in a sample by flow cytometry comprising:

(a) mixing an aliquot of a blood sample with a reagent system comprising a red blood cell (RBC) lysing component and a vital nuclear stain component to stain the nuclei of the NRBC and any damaged WBC, wherein the lysing component lyses RBC while minimizing damage to WBC cellular membranes and WBC surface antigens;

(b) passing the mixed aliquot, substantially a cell at a time, through an area of optical stimulation;

(c) obtaining at least one signal for the parameter of fluorescence (FL) and at least one signal for the parameter of scattered light at a range of scatter angles comprising from about 0° to about 1° and about 3°–10°;

(d) qualifying the signals obtained by subjecting the signals to a logic wherein a signal to be qualified must be greater than a 3°–10° scatter signal threshold, while at the same time it must be greater than either a 0° to about 1° signal threshold or a FL threshold wherein the thresholds are set to eliminate spurious FL noise signals and include NRBC population signals in the signals obtained;

(e) constructing a three-dimensional plot of intensity signals of FL and scattered light from the obtained and qualified signals; and (f) differentiating WBC, NRBC, damaged WBC and a WBC subclass differential (WBC/Diff) from the constructed three-dimensional plot and the qualified signals and determining the number of cells of each.

3. The method of claim 2 wherein the nuclear stain is selected from the group consisting of propidium iodide (PI), ethidium bromide (EBr), ethidium homodimer-1 (EthD-1), ethidium homodimer-2 (EthD-2) and diethylene triamine (DTA).

4. The method of claim 2 further comprising the step of adding fluorescently labeled antibodies to the sample and incubating the antibody/sample mixing for a time sufficient for the antibodies to bind with their binding partner surface antigen prior to step (a).

5. The method of claim 2 wherein the determined NRBC count is subtracted from the determined WBC counts before determining the WBC/Diff.

* * * * *